United States Patent
Abbot et al.

(10) Patent No.: US 11,130,820 B2
(45) Date of Patent: *Sep. 28, 2021

(54) CHIMERIC ANTIGEN RECEPTORS

(71) Applicant: CELGENE CORPORATION, Summit, NJ (US)

(72) Inventors: Stewart Abbot, San Diego, CA (US); Bitao Liang, Closter, NJ (US); Tianjian Li, Belle Mead, NJ (US)

(73) Assignee: CELGENE CORPORATION, Summit, NJ (US)

( * ) Notice: Subject to any disclaimer, the term of this patent is extended or adjusted under 35 U.S.C. 154(b) by 179 days.

This patent is subject to a terminal disclaimer.

(21) Appl. No.: 16/175,747

(22) Filed: Oct. 30, 2018

(65) Prior Publication Data

US 2019/0119399 A1 Apr. 25, 2019

Related U.S. Application Data

(63) Continuation of application No. 14/653,650, filed as application No. PCT/US2013/076486 on Dec. 19, 2013, now Pat. No. 10,150,816.

(60) Provisional application No. 61/779,925, filed on Mar. 13, 2013, provisional application No. 61/740,113, filed on Dec. 20, 2012.

(51) Int. Cl.
*C07K 16/30* (2006.01)
*C07K 14/705* (2006.01)
*C07K 14/725* (2006.01)
*C07K 16/28* (2006.01)

(52) U.S. Cl.
CPC ...... *C07K 16/3069* (2013.01); *C07K 14/7051* (2013.01); *C07K 14/70503* (2013.01); *C07K 14/70521* (2013.01); *C07K 16/2803* (2013.01); *C07K 16/30* (2013.01); *C07K 16/3061* (2013.01); *C07K 2317/622* (2013.01); *C07K 2319/00* (2013.01); *C07K 2319/03* (2013.01); *C07K 2319/33* (2013.01)

(58) Field of Classification Search
CPC . C07K 2319/03; C07K 2319/00; C12N 15/62
See application file for complete search history.

(56) References Cited

U.S. PATENT DOCUMENTS

| | | | |
|---|---|---|---|
| 4,554,101 A | 11/1985 | Hopp | |
| 4,798,824 A | 1/1989 | Belzer et al. | |
| 4,873,192 A | 10/1989 | Kunkel | |
| 5,283,173 A | 2/1994 | Fields et al. | |
| 5,372,581 A | 12/1994 | Anderson | |
| 5,415,665 A | 5/1995 | Hessel et al. | |
| 5,468,614 A | 11/1995 | Fields et al. | |
| 5,552,267 A | 9/1996 | Stern et al. | |
| 5,593,990 A | 1/1997 | D'Amato | |
| 5,629,327 A | 5/1997 | D'Amato | |
| 5,635,517 A | 6/1997 | Muller et al. | |
| 5,665,577 A | 9/1997 | Sodroski et al. | |
| 5,677,171 A | 10/1997 | Finn et al. | |
| 5,686,281 A | 11/1997 | Roberts | |
| 5,698,520 A | 12/1997 | Honjo et al. | |
| 5,698,579 A | 12/1997 | Muller | |
| 5,712,149 A | 1/1998 | Roberts | |
| 5,720,937 A | 2/1998 | Hudziak et al. | |
| 5,720,954 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,783,404 A | 7/1998 | Koski | |
| 5,798,368 A | 8/1998 | Muller et al. | |
| 5,827,642 A | 10/1998 | Riddell et al. | |
| 5,843,728 A | 12/1998 | Seed et al. | |
| 5,858,358 A | 1/1999 | June et al. | |
| 5,874,448 A | 2/1999 | Muller et al. | |
| 5,877,200 A | 3/1999 | Muller | |
| 5,883,223 A | 3/1999 | Gray | |
| 5,906,936 A | 5/1999 | Eshhar et al. | |
| 5,929,117 A | 7/1999 | Muller et al. | |
| 5,948,893 A | 9/1999 | June et al. | |
| 5,977,318 A | 11/1999 | Linsley et al. | |

(Continued)

FOREIGN PATENT DOCUMENTS

| | | |
|---|---|---|
| CN | 1764471 A | 4/2006 |
| CN | 101563104 A | 10/2009 |

(Continued)

OTHER PUBLICATIONS

Abaza et al., 1992, "Effects of amino acid substitutions outside an antigenic site on protein binding to monoclonal antibodies of predetermined specificity obtained by peptide immunization: demonstration with region 94-100 (antigenic site 3) of myoglobin," J. Protein Chem., 11(5):433-444.

(Continued)

*Primary Examiner* — Peter J Reddig
(74) *Attorney, Agent, or Firm* — Morrison & Foerster LLP

(57) ABSTRACT

Provided herein are therapeutic polypeptides, e.g., chimeric antigen receptors, able to direct an immune cell, e.g., a T lymphocyte to a target antigen, and able to cause the T cell to proliferate or to kill cells displaying the antigen when the antigen binds to the polypeptide, wherein the polypeptides comprise a transmembrane domain from a T cell co-inhibitory protein such as CTLA4 or PD-1. Also provided herein are T lymphocytes expressing the polypeptides, and use of such T lymphocytes to treat diseases such as cancer.

12 Claims, 11 Drawing Sheets

Specification includes a Sequence Listing.

(56) References Cited

U.S. PATENT DOCUMENTS

| | | |
|---|---|---|
| 5,994,136 A | 11/1999 | Naldini et al. |
| 6,005,079 A | 12/1999 | Casterman et al. |
| 6,013,516 A | 1/2000 | Verma et al. |
| 6,040,177 A | 3/2000 | Riddell et al. |
| 6,071,948 A | 6/2000 | D'Amato |
| 6,103,521 A | 8/2000 | Capon et al. |
| 6,165,464 A | 12/2000 | Hudziak et al. |
| 6,165,782 A | 12/2000 | Naldini et al. |
| 6,281,230 B1 | 8/2001 | Muller et al. |
| 6,316,471 B1 | 11/2001 | Muller et al. |
| 6,319,494 B1 | 11/2001 | Capon et al. |
| 6,335,349 B1 | 1/2002 | Muller et al. |
| 6,352,694 B1 | 3/2002 | June et al. |
| 6,355,699 B1 | 3/2002 | Vyakarnam et al. |
| 6,387,371 B1 | 5/2002 | Hudziak et al. |
| 6,399,063 B1 | 6/2002 | Hudziak et al. |
| 6,410,319 B1 | 6/2002 | Raubitschek et al. |
| 6,428,953 B1 | 8/2002 | Naldini et al. |
| 6,476,052 B1 | 11/2002 | Muller et al. |
| 6,534,055 B1 | 3/2003 | June et al. |
| 6,682,907 B1 | 1/2004 | Charneau et al. |
| 6,692,964 B1 | 2/2004 | June et al. |
| 6,756,036 B2 | 6/2004 | Reiter et al. |
| 6,790,939 B2 | 9/2004 | Reiter et al. |
| 6,797,514 B2 | 9/2004 | Berenson et al. |
| 6,825,326 B2 | 11/2004 | Reiter et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,045,148 B2 | 5/2006 | Hariri |
| 7,052,906 B1 | 5/2006 | Lawson et al. |
| 7,067,318 B2 | 6/2006 | June et al. |
| 7,070,995 B2 | 7/2006 | Jensen |
| 7,083,981 B2 | 8/2006 | Naldini et al. |
| 7,091,353 B2 | 8/2006 | Robarge et al. |
| 7,144,575 B2 | 12/2006 | June et al. |
| 7,147,626 B2 | 12/2006 | Goodman et al. |
| 7,172,869 B2 | 2/2007 | June et al. |
| 7,175,843 B2 | 2/2007 | June et al. |
| 7,232,566 B2 | 6/2007 | June et al. |
| 7,250,299 B1 | 7/2007 | Naldini et al. |
| 7,255,879 B2 | 8/2007 | Hariri |
| 7,265,209 B2 | 9/2007 | Jensen |
| 7,344,715 B2 | 3/2008 | Raison et al. |
| 7,407,656 B2 | 8/2008 | Reiter et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,462,352 B2 | 12/2008 | Hansen et al. |
| 7,468,276 B2 | 12/2008 | Hariri |
| 7,485,296 B2 | 2/2009 | Reiter et al. |
| 7,514,537 B2 | 4/2009 | Jensen |
| 7,527,786 B2 | 5/2009 | Reiter et al. |
| 7,541,442 B2 | 6/2009 | Gudas et al. |
| 7,556,803 B2 | 7/2009 | Raison et al. |
| 7,595,379 B2 | 9/2009 | Gudas et al. |
| 7,655,461 B2 | 2/2010 | Finn et al. |
| 7,662,378 B2 | 2/2010 | Goldenberg et al. |
| 7,736,644 B2 | 6/2010 | Weber et al. |
| 7,741,465 B1 | 6/2010 | Eshhar et al. |
| 7,902,338 B2 | 3/2011 | Hansen et al. |
| 7,919,090 B2 | 4/2011 | Goldenberg et al. |
| 7,951,369 B2 | 5/2011 | Goldenberg et al. |
| 8,057,788 B2 | 11/2011 | Hariri |
| 8,062,636 B2 | 11/2011 | Goldenberg et al. |
| 8,088,908 B2 | 1/2012 | Sherman et al. |
| 8,147,831 B2 | 4/2012 | Hansen et al. |
| 8,211,422 B2 | 7/2012 | Eshhar et al. |
| 8,216,572 B2 | 7/2012 | Goldenberg et al. |
| 8,263,065 B2 | 9/2012 | Hariri et al. |
| 8,287,865 B2 | 10/2012 | Hansen et al. |
| 8,324,353 B2 | 12/2012 | Jensen et al. |
| 8,399,645 B2 | 3/2013 | Campana et al. |
| 8,404,817 B2 | 3/2013 | Sherman et al. |
| 8,444,973 B2 | 5/2013 | Tedder et al. |
| 8,465,743 B2 | 6/2013 | Rosenberg et al. |
| 8,497,118 B2 | 7/2013 | Jensen |
| 8,530,168 B2 | 9/2013 | Chu et al. |
| 8,822,647 B2 | 9/2014 | Jensen |
| 9,469,684 B2 | 10/2016 | Finn et al. |
| 9,828,361 B2 | 11/2017 | Man et al. |
| 10,150,816 B2 * | 12/2018 | Abbot ................ C07K 16/3069 |
| 10,238,690 B2 | 3/2019 | Abbot et al. |
| 2002/0022676 A1 | 2/2002 | He et al. |
| 2003/0045552 A1 | 3/2003 | Robarge et al. |
| 2003/0096841 A1 | 5/2003 | Robarge et al. |
| 2003/0105000 A1 | 6/2003 | Pero et al. |
| 2003/0147869 A1 | 8/2003 | Riley et al. |
| 2003/0157713 A1 | 8/2003 | Ohno et al. |
| 2003/0235909 A1 | 12/2003 | Hariri et al. |
| 2004/0048796 A1 | 3/2004 | Hariri et al. |
| 2005/0118185 A1 | 6/2005 | Hombach et al. |
| 2006/0121005 A1 | 6/2006 | Berenson et al. |
| 2007/0190042 A1 | 8/2007 | Edinger et al. |
| 2007/0275362 A1 | 11/2007 | Edinger et al. |
| 2008/0102027 A1 | 5/2008 | Dunn et al. |
| 2009/0081172 A1 | 3/2009 | Finn et al. |
| 2009/0104164 A1 | 4/2009 | Zhang et al. |
| 2009/0155282 A1 | 6/2009 | Weber et al. |
| 2009/0156790 A1 | 6/2009 | Weber et al. |
| 2010/0105136 A1 | 4/2010 | Carter et al. |
| 2010/0135974 A1 | 6/2010 | Eshhar et al. |
| 2010/0215651 A1 | 8/2010 | Blein et al. |
| 2011/0023137 A1 | 1/2011 | Chu et al. |
| 2011/0229461 A1 | 9/2011 | Tyson et al. |
| 2011/0286980 A1 | 11/2011 | Brenner |
| 2012/0034245 A9 | 2/2012 | Thompson et al. |
| 2012/0093842 A1 | 4/2012 | Eshhar et al. |
| 2012/0148552 A1 | 6/2012 | Jensen |
| 2012/0148553 A1 | 6/2012 | Hariri et al. |
| 2012/0321667 A1 | 12/2012 | Sentman |
| 2013/0071414 A1 | 3/2013 | Dotti et al. |
| 2013/0084294 A1 | 4/2013 | Tedder et al. |
| 2013/0289261 A1 | 10/2013 | Finn et al. |
| 2013/0323834 A1 | 12/2013 | Brenner |
| 2014/0023647 A1 | 1/2014 | Slawin et al. |
| 2014/0087468 A1 | 3/2014 | Spencer et al. |
| 2014/0162282 A1 | 6/2014 | Schafer et al. |
| 2014/0286987 A1 | 9/2014 | Spencer et al. |
| 2014/0294784 A1 | 10/2014 | Waldman et al. |
| 2014/0322183 A1 | 10/2014 | Milone et al. |
| 2015/0291562 A1 | 10/2015 | Crew et al. |
| 2015/0307623 A1 | 10/2015 | Abbot et al. |
| 2015/0368360 A1 | 12/2015 | Liang et al. |
| 2016/0030479 A1 | 2/2016 | Abbot et al. |
| 2016/0151465 A1 | 6/2016 | Slawin et al. |
| 2016/0264665 A1 | 9/2016 | Lim et al. |
| 2018/0021378 A1 | 1/2018 | Kang et al. |
| 2018/0080008 A1 | 3/2018 | Liang et al. |
| 2018/0273640 A1 | 9/2018 | Liang et al. |
| 2019/0175652 A1 | 6/2019 | Abbot et al. |
| 2019/0240304 A1 | 8/2019 | Xu |
| 2021/0008109 A1 | 1/2021 | Kang et al. |

FOREIGN PATENT DOCUMENTS

| | | |
|---|---|---|
| CN | 103483452 A | 1/2014 |
| EP | 404097 B1 | 9/1996 |
| JP | A 2003-500021 | 1/2003 |
| JP | 2004113062 A | 4/2004 |
| JP | 2004529636 A | 9/2004 |
| JP | 2005336062 A | 12/2005 |
| JP | 2006518984 A | 8/2006 |
| JP | 2010531638 A | 9/2010 |
| WO | WO 1992008796 A1 | 5/1992 |
| WO | WO 1993001161 A1 | 1/1993 |
| WO | WO 1994004678 A1 | 3/1994 |
| WO | WO 1994025591 A1 | 11/1994 |
| WO | WO 1994028143 A1 | 12/1994 |
| WO | WO 1996005309 A2 | 2/1996 |
| WO | WO 1996023814 A1 | 8/1996 |
| WO | WO 1998003502 A1 | 1/1998 |

(56) References Cited

FOREIGN PATENT DOCUMENTS

| | | |
|---|---|---|
| WO | WO 2000063373 A1 | 10/2000 |
| WO | WO 2002033101 A1 | 4/2002 |
| WO | WO 2002059106 A1 | 8/2002 |
| WO | WO 2002077029 A2 | 10/2002 |
| WO | WO 2002077029 A3 | 10/2002 |
| WO | WO 2002088346 A2 | 11/2002 |
| WO | WO 2002088346 A3 | 11/2002 |
| WO | WO 2003057171 A2 | 7/2003 |
| WO | WO 2003057171 A3 | 7/2003 |
| WO | WO 2004039840 A1 | 5/2004 |
| WO | WO 2004084931 A1 | 10/2004 |
| WO | WO 2006010834 A1 | 2/2006 |
| WO | WO 2007089871 A2 | 8/2007 |
| WO | WO 2007089871 A3 | 8/2007 |
| WO | WO 2008150853 A1 | 12/2008 |
| WO | WO 2008154644 A1 | 12/2008 |
| WO | WO 2010003002 A2 | 1/2010 |
| WO | WO 2010003002 A3 | 1/2010 |
| WO | WO 2010003002 A9 | 1/2010 |
| WO | WO 2010104949 A2 | 9/2010 |
| WO | WO 2010104949 A3 | 9/2010 |
| WO | WO 2010108126 A2 | 9/2010 |
| WO | WO 2010108126 A3 | 9/2010 |
| WO | WO 2011035018 A2 | 3/2011 |
| WO | WO 2011160119 A2 | 12/2011 |
| WO | WO 2011160119 A3 | 12/2011 |
| WO | WO 2011160119 A8 | 12/2011 |
| WO | WO 2012033885 A1 | 3/2012 |
| WO | WO 2012050374 A2 | 4/2012 |
| WO | WO 2012058460 A2 | 5/2012 |
| WO | WO 2012058460 A3 | 5/2012 |
| WO | WO 2012079000 A1 | 6/2012 |
| WO | WO 2012099973 A2 | 7/2012 |
| WO | WO 2012099973 A3 | 7/2012 |
| WO | WO 2012129514 A1 | 9/2012 |
| WO | WO 2012138475 A1 | 10/2012 |
| WO | WO 2012138858 A1 | 10/2012 |
| WO | WO 2013040557 A2 | 3/2013 |
| WO | WO 2013040557 A3 | 3/2013 |
| WO | WO 2013059593 A1 | 4/2013 |
| WO | WO 2013063419 A2 | 5/2013 |
| WO | WO 2013063419 A3 | 5/2013 |
| WO | WO 2013067492 A1 | 5/2013 |
| WO | WO 2013070468 A1 | 5/2013 |
| WO | WO 2013123061 A1 | 8/2013 |
| WO | WO 2013188427 A1 | 12/2013 |
| WO | WO 2014028453 A2 | 2/2014 |
| WO | WO 2014028453 A3 | 2/2014 |
| WO | WO 2014037422 A1 | 3/2014 |
| WO | WO 2014055657 A1 | 4/2014 |
| WO | WO 2014055668 A1 | 4/2014 |
| WO | WO 2014100385 A1 | 6/2014 |
| WO | WO 2014124143 A1 | 8/2014 |
| WO | WO 2014145252 A2 | 9/2014 |
| WO | WO 2014152177 A1 | 9/2014 |
| WO | WO 2014164348 A2 | 10/2014 |
| WO | WO 2014197638 A2 | 12/2014 |
| WO | WO 2015127351 A1 | 8/2015 |
| WO | WO 2016007506 A1 | 1/2016 |
| WO | WO 2016025454 A2 | 2/2016 |
| WO | WO 2016025454 A3 | 2/2016 |
| WO | WO 2016109668 A1 | 7/2016 |
| WO | WO 2018075820 A2 | 4/2018 |
| WO | WO 2018075820 A3 | 4/2018 |
| WO | WO 2018085690 A1 | 5/2018 |
| WO | WO 2020014333 A1 | 1/2020 |

OTHER PUBLICATIONS

Bedzyke et al., 1990, "Immunological and structural characterization of a high affinity anti-fluorescein single-chain antibody," J. Biol Chem., 265(30):18615-18620.
Burgess et al., 1990, "Possible dissociation of the heparin-binding and mitogenic activities of heparin-binding (acidic fibroblast) growth factor-1 from its receptor-binding activities by site-directed mutagenesis of a single lysine residue," J. Cell Biol., 111(5 Pt 1):2129-2138.
Dobson et al., "The human transmembrane proteome," Biol. Direct., 2015, 10:31, pp. 1-18.
European Extended Search Report and Search Opinion dated Jun. 8, 2016 for EP Application No. 13865885.1.
Fedorov et al., 2013, "PD-1- and CTLA-4-based inhibitory chimeric antigen receptors (iCARs) divert off-target immunotherapy responses," Sci. Transl. Med. 5(215):1-13.
Fitzer-Attas et al., "Harnessing Syk family tyrosine kinases as signaling domains for chimeric single chain of the variable domain receptors: optimal design for T cell activation," J. Immunol., 1998, 160(1):145-154, The American Association of Immunologists, Inc., Rockville, MD, USA.
Harper et al., 1991, "CTLA-4 and CD28 activated lymphocyte molecules are closely related in both mouse and human as to sequence, message expression, gene structure, and chromosomal location," J. Immunol., 147(3):1037-1044.
Hyrup and Nielsen, 1996, "Peptide nucleic acids (PNA): synthesis, properties and potential applications," Bioorg. & Med. Chem., 4(1):5-23.
Ibragimova et al., 1999, "Stability of the beta-sheet of the WW domain: A molecular dynamics simulation study," Biophys J., 77(4):2191-2198.
Lázár-Molnár et al., 2008, "Crystal structure of the complex between programmed death-1 (PD-1) and its ligand PD-L2," Proc. Natl. Acad. Sci. USA, 105(30):10483-10488.
Rudikoff et al., 1982, "Single amino acid substitution altering antigen-binding specificity," Proc. Natl. Acad. Sci. USA, 79(6):1979-1983.
Shi et al., 2014, "Chimeric antigen receptor for adoptive immunotherapy of cancer: latest research and future prospects," Mol. Cancer, vol. 13—Issue 219, pp. 1-8.
Shin et al., 2012, "Positive conversion of negative signaling of CTLA4 potentiates antitumor efficacy of adoptive T-cell therapy in murine tumor models," Blood, 119(24):5678-5687.
Straathof et al., 2005, "An inducible caspase 9 safety switch for T-cell therapy," Blood, 105(11):4247-4254.
Summerton and Weller, 1997, "Morpholino antisense oligomers: design, preparation, and properties," Antisense Nucleic Acid Drug Dev, 7(3):187-95.
Van Der Stegen et al., 2015, "The pharmacology of second-generation chimeric antigen receptors," Nat Rev Drug Discov., 14(7):499-509.
Written Opinion and International Search Report dated Mar. 6, 2014 of PCT Application No. PCT/US2013/076486 filed Dec. 19, 2013 (WO 2014/100385).
European Search Report and Search Opinion dated Feb. 14, 2019 for EP Application No. 18195425.6 (7 pages).
Ali et al., 2016, "T cells expressing an anti-B-cell maturation antigen chimeric antigen receptor cause remissions of multiple myeloma," Blood, 128(13):1688-1700.
Allikmets et al., 1998, "A human placenta-specific ATP-binding cassette gene (ABCP) on chromosome 4q22 that is involved in multidrug resistance," Cancer Res., 58(23):5337-5339.
Altschul et al., 1997, "Gapped BLAST and PSI-BLAST: a new generation of protein database search programs," Nucleic Acids Res., 25(17):3389-3402.
Ansel et al., 1999, "In vivo-activated CD4 T cells upregulate CXC chemokine receptor 5 and reprogram their response to lymphoid chemokines," J Exp Med., 190(8):1123-1134.
Anseth et al., 2002, "In situ forming degradable networks and their application in tissue engineering and drug delivery," J Control Release, 78(1-3):199-209.
Asai et al., 2013, "Co-introduced functional CCR2 potentiates in vivo anti-lung cancer functionality mediated by T cells double gene-modified to express WT1-specific T-cell receptor," PLoS One, 8(2):e56820.
Asheuer et al., 2004, "Human CD34+ cells differentiate into microglia and express recombinant therapeutic protein," Proc Natl Acad Sci USA, 101(10):3557-3562.

(56) References Cited

OTHER PUBLICATIONS

Avery et al., 2003, "BAFF selectively enhances the survival of plasmablasts generated from human memory B cells," J Clin Invest., 112(2):286-297.
Bakdash et al., 2013, "Harnessing dendritic cells to promote immune tolerance: Opportunities for allergen-specific immunotherapy—Chapter 6: Retinoic acid primes human dendritic cells to induce gut-homing, IL-10 producing regulatory T cells," University of Amsterdam, Ph.D. Thesis, pp. 107-136.
Bakdash et al., 2013, "Intradermal application of vitamin D3 increases migration of CD14+ dermal dendritic cells and promotes the development of Foxp3+ regulatory T cells," Hum. Vaccin. Immunother., 9(2):250-258.
Bakdash, 2013, "Harnessing Dendritic Cells to Promote Immunite Tolerance: Opportunities for Allergen-Specific Immunotherapy," University of Amsterdam, Ph.D. Thesis, retreived from internet: dare.uva.nl/record/1/394938 (169 pages).
Banissi et al., 2009, "Treg depletion with a low-dose metronomic temozolomide regimen in a rat glioma model," Cancer Immunol Immunother, 58(10):1627-1634.
Bell et al., 1999, "The protein CTCF is required for the enhancer blocking activity of vertebrate insulators," Cell, 98(3):387-396.
Bellucci et al., 2005, "Graft-versus-tumor response in patients with multiple myeloma is associated with antibody response to BCMA, a plasma-cell membrane receptor," Blood, 105(10):3945-3950.
Benson et al., 2010, "The PD-1/PD-L1 axis modulates the natural killer cell versus multiple myeloma effect: a therapeutic target for CT-011, a novel monoclonal anti-PD-1 antibody," Blood, 116(13):2286-2294.
Berdeja et al., 2016, "Clinical remissions and limited toxicity in a first-in-human multicenter study of bb2121, a novel anti-BCMA CAR T cell therapy for relapsed/refractory multiple myeloma," European Journal of Cancer, S5, Abstract 14LBA (1 page).
Berdeja et al., 2017, "Durable clinical responses in heavily pre-treated patients with relapsed/refractory multiple myeloma: Updated results from a multicenter study of bb2121 anti-BCMA CAR T cell therapy," Blood, 130:740 (7 pages).
Bird et al., 1988, "Single-chain antigen-binding proteins," Science, 242(4877):423-426.
Bissonnetie et al., 1994, "Functional Myc-Max heterodimer is required for activation-induced apoptosis in T cell hybridomas", J Exp Med., 180(6):2413-2418.
Bogen et al., 2004, "Recent Trends and Advances in Immunodiagnostics of Solid Tumors," BioDrugs, 18(6):387-398.
Borden et al., 1987, "Nucleotide sequence of the cDNAs encoding the variable region heavy and light chains of a myeloma protein specific for the terminal nonreducing end of alpha(1—>6)dextran," Proc Natl Acad Sci USA, 84(8):2440-2443.
Burgess-Beusse et al., 2002, "The insulation of genes from external enhancers and silencing chromatin," Proc Natl Acad Sci USA, 99 Suppl 4(Suppl 4):16433-16437.
Camicia et al., 2015, "Novel drug targets for personalized precision medicine in relapsed/refractory diffuse large B-cell lymphoma: a comprehensive review," Mol. Cancer, 14:207, pp. 1-62.
Cany et al., 2013, "Natural killer cells generated from cord blood hematopoietic progenitor cells efficiently target bone marrow-residing human leukemia cells in NOD/SCID/IL2Rg(null) mice," PLoS One, 8(6):e64384.
Carpenito et al., 2009, "Control of large, established tumor xenografts with genetically retargeted human T cells containing CD28 and CD137 domains," Proc Natl Acad Sci USA, 106(9):3360-3365.
Carpenter et al., 2013, "B-cell maturation antigen is a promising target for adoptive T-cell therapy of multiple myeloma," Clin Cancer Res., 19(8):2048-2060.
Challita et al., 1995, "Multiple modifications in cis elements of the long terminal repeat of retroviral vectors lead to increased expression and decreased DNA methylation in embryonic carcinoma cells," J Virol., 69(2):748-755.

Chaudhary et al., 1990, "A rapid method of cloning functional variable-region antibody genes in *Escherichia coli* as single-chain immunotoxins," Proc Natl Acad Sci USA, 87(3):1066-1070.
Chiu et al., 2007, "Hodgkin lymphoma cells express TACI and BCMA receptors and generate survival and proliferation signals in response to BAFF and APRIL," Blood, 109(2):729-739 (Epub Sep. 7, 2006).
Chmielewski et al., 2012, "T cells that target carcinoembryonic antigen eradicate orthotopic pancreatic carcinomas without inducing autoimmune colitis in mice," Gastroenterology, 143(4):1095-1107.e2.
Chmielewski et al., 2012, "CAR's made it to the pancreas," Oncoimmunology 1(8):1387-1389.
Chothia et al., 1987, "Canonical structures for the hypervariable regions of immunoglobulins," J Mol Biol., 196(4):901-917.
Chothia et al., 1989, "Conformations of immunoglobulin hypervariable regions," Nature, 342(6252):877-883.
Chung et al., 1993, "A 5' element of the chicken beta-globin domain serves as an insulator in human erythroid cells and protects against position effect in *Drosophila*," Cell, 74(3):505-514.
Chung et al., 1997, "Characterization of the chicken beta-globin insulator," Proc Natl Acad Sci USA, 94(2):575-580.
Clever et al., 1995, "RNA secondary structure and binding sites for gag gene products in the 5' packaging signal of human immunodeficiency virus type 1," J Virol., 69(4):2101-2109.
ClinicalTrials.gov Identifier: NCT02658929, "Study of bb2121 in Multiple Myeloma," First Posted: Jan. 20, 2016, Last Update Posted: Aug. 21, 2019 (12 pages).
ClinicalTrials.gov Identifier: NCT03361748, "Efficacy and Safety Study of bb2121 in Subjects With Relapsed and Refractory Multiple Myeloma (KarMMa) (KarMMa)," First Posted: Dec. 5, 2017, Last Update Posted: Sep. 11, 2019 (2 pages).
Cooper et al., 2003, "T-cell clones can be rendered specific for CD19: toward the selective augmentation of the graft-versus-B-lineage leukemia effect," Blood, 101(4):1637-1644 (Epub Oct. 10, 2002).
Craddock et al., 2010, "Enhanced tumor trafficking of GD2 chimeric antigen receptor T cells by expression of the chemokine receptor CCR2b," J Immunother, 33(8):780-788.
Cullen et al., 1989, Regulatory pathways governing HIV-1 replication, Cell, 58(3):423-426.
Cullen, 1991, "Human immunodeficiency virus as a prototypic complex retrovirus," J Virol., 65(3):1053-1056.
Davila et al., 2014, "Chimeric Antigen Receptors for the Adoptive T Cell Therapy of Hematologic Malignancies," Int J Hematol., 99(4):361-371 (Epub 2013).
De Felipe et al., 2004, "Targeting of proteins derived from self-processing polyproteins containing multiple signal sequences," Traffic, 5(8):616-626.
Desjarlais et al., 1993, "Use of a zinc-finger consensus sequence framework and specificity rules to design specific DNA binding proteins," Proc Natl Acad Sci USA, 90(6):2256-2260.
Desjarlais et al., 1994, "Length-encoded multiplex binding site determination. application to zinc finger proteins," Proc Natl Acad Sci USA, 91(23):11099-11103.
Di Stasi et al., 2009, "T lymphocytes coexpressing CCR4 and a chimeric antigen receptor targeting CD30 have improved homing and antitumor activity in a Hodgkin tumor model," Blood, 113(25):6392-6402.
Di Stasi et al., 2011, "Inducible apoptosis as a safety switch for adoptive cell therapy", N. Engl. J. Med., 365(18):1673-1683.
Donnelly et al., 2001, "The 'cleavage' activities of foot-and-mouth disease virus 2A site-directed mutants and naturally occurring '2A-like' sequences," J Gen Virol., 82(Pt 5):1027-1041.
Duong et al., 2011, "Enhancing the specificity of T-cell cultures for adoptive immunotherapy of cancer," Immunotherapy, 3(1):33-48.
Edwards et al., 2003, "The remarkable flexibility of the human antibody repertoire; isolation of over one thousand different antibodies to a single protein, BLyS," J Mol Biol., 334(1):103-118.
Ercolini et al., 2005, "Recruitment of latent pools of high-avidity CD8(+) T cells to the antitumor immune response," J Exp Med., 201(10):1591-1602.

(56) References Cited

OTHER PUBLICATIONS

Ferlazzo et al., 2004, "The abundant NK cells in human secondary lymphoid tissues require activation to express killer cell Ig-like receptors and become cytolytic," J Immunol., 172(3):1455-1462.
Fire et al., 1998, "Potent and specific genetic interference by double-stranded RNA in Caenorhabditis elegans," Nature, 391(6669):806-811.
Friedman et al., 2018, "Effective Targeting of Multiple B-Cell Maturation Antigen-Expressing Hematological Malignances by Anti-B-Cell Maturation Antigen Chimeric Antigen Receptor T Cells," Hum Gene Ther., 29(5):585-601.
Gandhi et al., 2014, "Immunomodulatory agents lenalidomide and pomalidomide co-stimulate T cells by inducing degradation of T cell repressors Ikaros and Aiolos via modulation of the E3 ubiquitin ligase complex CRL4$^{CRBN}$," Br. J. Haematol., 164(6):811-821. [First published online Dec. 13, 2013].
GenBank Accession No. AA107160.1, "m157d12.r1 Stratagene mouse testis (#937308) Mus musculus cDNA clone IMAGE:516119 5' similar to TR:G600529 G600529 NADH Ubiquinone Oxidoreductase Subunit, mRNA sequence" (Feb. 3, 1997).
GenBank Accession No. BC107159.1, "*Homo sapiens* chemokine (C-C motif) receptor 8, mRNA (cDNA clone MGC:129973 IMAGE:40032938), complete cds" (Oct. 4, 2006).
GenBank Accession No. NM_000885.4, "*Homo sapiens* integrin, alpha 4 (antigen CD49D, alpha 4 subunit of VLA-4 receptor) (ITGA4), mRNA" (Mar. 15, 2015).
GenBank Accession No. NM_000889.2, "*Homo sapiens* integrin subunit beta 7 (ITGB7), transcript variant 1, mRNA" (Jun. 30, 2018).
GenBank Accession No. NM_001008540.1, "*Homo sapiens* C-X-C motif chemokine receptor 4 (CXCR4), transcript variant 1, mRNA" (Dec. 21, 2016).
GenBank Accession No. NM_001206609.1, "*Homo sapiens* selectin P ligand (SELPLG), transcript variant 1, mRNA" (Oct. 13, 2018).
GenBank Accession No. NM_001256369.1, "*Homo sapiens* C-C motif chemokine receptor 9 (CCR9), transcript variant C, mRNA" (Jun. 3, 2018).
GenBank Accession No. NM_001301714.1, "*Homo sapiens* C-C motif chemokine receptor 7 (CCR7), transcript variant 2, mRNA" (Apr. 2, 2019).
GenBank Accession No. NM_001301716.1, "*Homo sapiens* C-C motif chemokine receptor 7 (CCR7), transcript variant 3, mRNA" (Apr. 2, 2019).
GenBank Accession No. NM_001301717.1, "*Homo sapiens* C-C motif chemokine receptor 7 (CCR7), transcript variant 4, mRNA" (Apr. 2, 2019).
GenBank Accession No. NM_001301718.1, "*Homo sapiens* C-C motif chemokine receptor 7 (CCR7), transcript variant 5, mRNA" (Apr. 2, 2019).
GenBank Accession No. Nm 001716.4, "*Homo sapiens* C-X-C motif chemokine receptor 5 (CXCR5), transcript variant 1, mRNA" (Apr. 9, 2019).
GenBank Accession No. NM_001838.3, "*Homo sapiens* C-C motif chemokine receptor 7 (CCR7), transcript variant 1, mRNA" (Jun. 3, 2018).
GenBank Accession No. NM_002253.2, "*Homo sapiens* kinase insert domain receptor (KDR), mRNA". (Dec. 18, 2017).
GenBank Accession No. NM_003006.4, "*Homo sapiens* selectin P ligand (SELPLG), transcript variant 2, mRNA" (Feb. 23, 2019).
GenBank Accession No. NM_003467.2, "*Homo sapiens* C-X-C motif chemokine receptor 4 (CXCR4), transcript variant 2, mRNA" (Apr. 23, 2019).
GenBank Accession No. NM_005201.3, "*Homo sapiens* C-C motif chemokine receptor 8 (CCR8), mRNA" (Feb. 18, 2019).
GenBank Accession No. NM_005508.4, "*Homo sapiens* C-C motif chemokine receptor 4 (CCR4), mRNA" (Mar. 25, 2019).
GenBank Accession No. NM_016602.2, "*Homo sapiens* C-C motif chemokine receptor 10 (CCR10), mRNA" (Jun. 24, 2018).
GenBank Accession No. NM_031200.2, "*Homo sapiens* C-C motif chemokine receptor 9 (CCR9), transcript variant A, mRNA" (Jun. 3, 2018).
GenBank Accession No. NM_032966.2, "*Homo sapiens* C-X-C motif chemokine receptor 5 (CXCR5), transcript variant 2, mRNA" (Apr. 9, 2019).
GenBank Accession No. NP_000876.3, "integrin alpha-4 isoform 1 preproprotein [*Homo sapiens*]" (Feb. 10, 2019).
GenBank Accession No. NP_000880.1, "integrin beta-7 precursor [*Homo sapiens*]" (Mar. 25, 2019).
GenBank Accession No. NP_001008540.1, "C-X-C chemokine receptor type 4 isoform a [*Homo sapiens*]" (Apr. 23, 2019).
GenBank Accession No. NP_001193538.1, "P-selectin glycoprotein ligand 1 isoform 1 precursor [*Homo sapiens*]" (Oct. 13, 2018).
GenBank Accession No. NP_001243298.1, "C-C chemokine receptor type 9 isoform B [*Homo sapiens*]" (Jun. 3, 2018).
GenBank Accession No. NP_001288643.1, "C-C chemokine receptor type 7 isoform b [*Homo sapiens*]" (Apr. 2, 2019).
GenBank Accession No. NP_001288645.1, "C-C chemokine receptor type 7 isoform c precursor [*Homo sapiens*]" (Apr. 2, 2019).
GenBank Accession No. NP_001288646.1, "C-C chemokine receptor type 7 isoform c precursor [*Homo sapiens*]" (Apr. 2, 2019).
GenBank Accession No. NP_001288647.1, "C-C chemokine receptor type 7 isoform c precursor [*Homo sapiens*]" (Apr. 2, 2019).
GenBank Accession No. NP_001829.1, "C-C chemokine receptor type 7 isoform a precursor [*Homo sapiens*]" (Apr. 2, 2019).
GenBank Accession No. NP_002244.1, "vascular endothelial growth factor receptor 2 precursor [*Homo sapiens*]" (Apr. 20, 2019).
GenBank Accession No. NP_002997.2, "P-selectin glycoprotein ligand 1 isoform 2 precursor [*Homo sapiens*]" (Feb. 23, 2019).
GenBank Accession No. NP_003458.1, "C-X-C chemokine receptor type 4 isoform b [*Homo sapiens*]" (Apr. 23, 2019).
GenBank Accession No. NP_005192.1, "C-C chemokine receptor type 8 [*Homo sapiens*]" (Feb. 18, 2019).
GenBank Accession No. NP_057686.2, "C-C chemokine receptor type 10 [*Homo sapiens*]" (Dec. 29, 2018).
GenBank Accession No. NP_112477.1, "C-C chemokine receptor type 9 isoform A [*Homo sapiens*]" (Feb. 10, 2019).
GenBank Accession No. NP_116743.1, "C-X-C chemokine receptor type 5 isoform 2 [*Homo sapiens*]" (Apr. 9, 2019).
GenBank Accession No. P46092.3, "RecName: Full=C-C chemokine receptor type 10; Short=C-C CKR-10; Short=CC-CKR-10; Short=CCR-10; AltName: Full=G-protein coupled receptor 2" (Apr. 10, 2019).
GenBank Accession No. P51679.1, "RecName: Full=C-C chemokine receptor type 4; Short=C-C CKR-4; Short=CC-CKR-4; Short=CCR-4; Short=CCR4; AltName: Full=K5-5; AltName: CD_antigen=CD194" (Apr. 10, 2019).
GenBank Gene ID: 10320, IKZF1 IKAROS family zinc finger 1 [*Homo sapiens* (human)], updated Aug. 6, 2019, retreived from https://www.ncbi.nlm.nih.gov/gene/10320 on Aug. 9, 2019.
GenBank Gene ID: 22806, IKZF3 Ikaros family zinc finger 3 [*Homo sapiens* (human)], updated Aug. 4, 2019, retreived from https://www.ncbi.nlm.nih.gov/gene/22806 on Aug. 9, 2019.
GenBank Gene ID: 51185, CRBN cereblon [*Homo sapiens* (human)], updated Jun. 17, 2019, retreived from https://www.ncbi.nlm.nih.gov/gene/51185 on Aug. 9, 2019.
Ghermezi et al., 2017, "Serum B-cell maturation antigen: a novel biomarker to predict outcomes for multiple myeloma patients," Haematologica, 102(4):785-795.
Gleason et al., 2012, "Bispecific and trispecific killer cell engagers directly activate human NK cells through CD16 signaling and induce cytotoxicity and cytokine production," Mol Cancer Ther., 11(12):2674-2684.
Gleason et al., 2014, "CD16xCD33 bispecific killer cell engager (BiKE) activates NK cells against primary MDS and MDSC CD33+ targets," Blood, 123(19):3016-3026.
Haanen eta l., 1999, "Selective expansion of cross-reactive CD8(+) memory T cells by viral variants," J Exp Med., 90(9):1319-1328.
Han et al., 2013, "Chimeric antigen receptor-engineered T cells for cancer immunotherapy: progress and challenges," J Hematol Oncol., 6:47 (7 pages).

(56) References Cited

OTHER PUBLICATIONS

Hegde et al., 2011, "Abstract 913: Targeting tumor heterogeneity in glioblastoma: bispecific T cells exhibit enhanced effector functions and offset antigen loss escape variants," American Society of Cell and Gene Therapy, 19(7):1388 (2 pages).
Holash et al., 2002, "VEGF-Trap: a VEGF blocker with potent antitumor effects," Proc. Natl. Acad. Sci. USA 99(17):11393-11398.
Holliger et al., 1993, "'Diabodies": small bivalent and bispecific antibody fragments," Proc Natl Acad Sci USA, 90(14):6444-6448.
Hoyos et al. 2012, "Genetic modification of human T lymphocytes for the treatment of hematologic malignancies," Haematologica, 97(11):1622-1631.
Huang et al., 2008, "Oral supplementation of lutein/zeaxanthin and omega-3 long chain polyunsaturated fatty acids in persons aged 60 years or older, with or without AMD," Invest Ophthalmol Vis Sci., 49(9):3864-3869.
Hudson et al., 2003, "Engineered antibodies," Nat Med., 9(1):129-134.
International Search Report and Written Opinion of International Patent Application No. PCT/US2014/015113 (Pub No. WO 2014124143) dated Jul. 9, 2014 (14 pages).
International Search Report and Written Opinion of International Patent Application No. PCT/US2015/044611 (Pub No. WO 2016025454) dated Jan. 21, 2016 (17 pages).
International Search Report and Written Opinion of International Patent Application PCT/US2015/068069 (Pub No. WO 2016109668) dated Mar. 31, 2016 (17 pages).
International Search Report and Written Opinion of International Patent Application No. PCT/US2017/057474 (Pub No. WO 2018075820) dated Jan. 22, 2018 (19 pages).
International Search Report and Written Opinion of International Patent Application No. PCT/US2019/041165 (Pub. No. WO 2020014333) dated Oct. 15, 2019 (16 pages).
International Search Report of International Patent Application No. PCT/US2014/027039 (Pub No. WO 2014152177) dated Jul. 7, 2014 (4 pages).
Introna et al., 2000, "Genetic modification of human T cells with CD20: a strategy to purify and lyse transduced cells with anti-CD20 antibodies," Hum. Gene Ther., 11(4):611-620.
Irion et al., 2007, "Identification and targeting of the ROSA26 locus in human embryonic stem cells," Nat Biotechnol, 25(12):1477-1482.
Jackson et al., 1995, "Internal initiation of translation in eukaryotes: the picornavirus paradigm and beyond," RNA, 1(10):985-1000.
Jena et al., 2010, "Redirecting T-cell specificity by introducing a tumor-specific chimeric antigen receptor," Blood, 116(7):1035-1044.
Kalled, 2005, "The role of BAFF in immune function and implications for autoimmunity" Immunol Rev., 204:43-54.
Kametaka et al., 2003, "Reduction of CTLL-2 cytotoxicity by induction of apoptosis with a Fas-estrogen receptor chimera", Cancer Sci., 94(7):639-643.
Kay, 1997, "Adenoviral vectors for hepatic gene transfer in animals," Chest, 111(6 Suppl):138S-142S.
Kershaw et al., 2002, "Redirecting migration of T cells to chemokine secreted from tumors by genetic modification with CXCR2," Hum. Gene Ther., 13(16):1971-1980.
Kershaw et al., 2013, "Gene-engineered T Cells for Cancer Therapy," Nat Rev Cancer, 13(8):525-541.
Kim et al., 1996, "Hybrid restriction enzymes: zinc finger fusions to Fok I cleavage domain," Proc Natl Acad Sci USA, 93(3):1156-1160.
Kloss et al., 2013, "Combinatorial antigen recognition with balanced signaling promotes selective tumor eradication by engineered T cells," Nat. Biotechnol., 31(1):71-75.
Kocoglu et al., 2016, "The Role of Immunotherapy in Multiple Myeloma," Pharmaceuticals (Basel), 9(1) (13 pages).
Koehler et al., 2012, "Engineered T cells for the adoptive therapy of B-cell chronic lymphocytic leukaemia," Advances in Hematology, vol. 2012, Article ID 595060 (13 pages).
Kozak, 1986, "Point mutations define a sequence flanking the AUG initiator codon that modulates translation by eukaryotic ribosomes," Cell, 44(2):283-292.
Kozak, 1987, "An analysis of 5'-noncoding sequences from 699 vertebrate messenger RNAs," Nucleic . Acids Res., 15(20):8125-8148.
Kunkel, 1985, "Rapid and efficient site-specific mutagenesis without phenotypic selection," Proc Natl Acad Sci USA, 82(2):488-492.
Laabi et al., 1992, "A new gene, BCM, on chromosome 16 is fused to the interleukin 2 gene by a t(4;16)(q26;p13) translocation in a malignant T cell lymphoma," EMBO J., 11(11):3897-3904.
Laabi et al. 1994, "The BCMA gene, preferentially expressed during B lymphoid maturation, is bidirectionally transcribed," Nucleic Acids Res., 22(7):1147-1154.
Landau et al., 1992, "Packaging system for rapid production of murine leukemia virus vectors with variable tropism," J Virol., 66(8):5110-5113.
Lee et al., 2000, "Remission in models of type 1 diabetes by gene therapy using a single-chain insulin analogue," Nature, 408(6811):483-488 and Retraction published Apr. 2, 2009.
Lehmann et al., 2012, "Ex vivo generated natural killer cells acquire typical natural killer receptors and display a cytotoxic gene expression profile similar to peripheral blood natural killer cells," Stem Cells Dev., 21(16):2926-2938.
Lin et al., 1999, "RNA interference. Policing rogue genes," Nature, 402(6758):128-129.
Litterman et al., 2013, "Profound impairment of adaptive immune responses by alkylating chemotherapy," J Immunol., 190(12):6259-6268.
Litwin et al., 1993, "Specificity of HLA class I antigen recognition by human Nk clones: evidence for clonal heterogeneity, protection by self and non-self alleles, and influence of the target cell type," J Exp Med., 178(4):1321-1336.
Liu et al., 1995, "HnRNP L binds a cis-acting RNA sequence element that enables intron-dependent gene expression," Genes Dev., 9(14):1766-1780.
Liu et al., 1997, "Design of polydactyl zinc-finger proteins for unique addressing within complex genomes," Proc Natl Acad Sci USA, 94(11):5525-5530.
Liu et al., 2009, "Targeting the phosphoinositide 3-kinase pathway in cancer," Nat Rev Drug Discov., 8(8):627-644.
Liu et al., 2011, "BAFF inhibition: a new class of drugs for the treatment of autoimmunity," Exp Cell Res., 317(9):1270-1277.
Lloyd et al., 2009, "Modelling the human immune response: performance of a 1011 human antibody repertoire against a broad panel of therapeutically relevant antigens," Protein Eng Des Sel., 22(3):159-168, Epub Oct. 29, 2008.
Lupton et al., 1991, "Dominant positive and negative selection using a hygromycin phosphotransferase-thymidine kinase fusion gene," Mol Cell Biol., 11(6):3374-3378.
Mackay et al., 2003, "BAFF and APRIL: a tutorial on B cell survival," Annu Rev Immunol., 21:231-264.
Maher, 2012, "Immunotherapy of malignant disease using chimeric antigen receptor engrafted T cells", ISRN Oncol., 2012:278093 (23 pages).
Majzner et al., 2018, "Tumor Antigen Escape from CAR T-cell Therapy," Cancer Discov., 8(10):1219-1226.
Maki et al., 2008, "MEK1/2 induces STAT5-mediated germline transcription of the TCRgamma locus in response to IL-7R signaling," J. Immunol. 181(1):494-502.
Mariuzza et al., 1987, "The structural basis of antigen-antibody recognition," Annu Rev Biophys Biophys Chem., 16:139-159.
Matsushita et al., 2005, "The role of BAFF in autoimmune diseases," Jpn. J. Clin. Immunol., 28(5):333-342 (in Japanese with English abstract).
Meuer et al., 1984, "An alternative pathway of T-cell activation: a functional role for the 50 kd T11 sheep erythrocyte receptor protein," Cell, 36(4):897-906.
Milone et al., 2009, "Chimeric receptors containing CD137 signal transduction domains mediate enhanced survival of T cells and increased antileukemic efficacy in vivo," Mol Ther., 17(8):1453-1464.

(56) References Cited

OTHER PUBLICATIONS

Montaldo et al., 2012, "Human NK cells at early stages of differentiation produce CXCL8 and express CD161 molecule that functions as an activating receptor," Blood, 119(17):3987-3996.
Moon et al., 2011, "Expression of a functional CCR2 receptor enhances tumor localization and tumor eradication by retargeted human T cells expressing a mesothelin-specific chimeric antibody receptor," Clin Cancer Res., 17(14):4719-4730.
Mora et al., 2008, "Vitamin effects on the immune system: vitamins A and D take centre stage," Nat Rev Immunol., 8(9):685-698.
Moreaux et al., 2004, "BAFF and APRIL protect myeloma cells from apoptosis induced by interleukin 6 deprivation and dexamethasone," Blood, 103(8):3148-3157 (Epub Dec. 4, 2003).
Morgan et al., 2010, "Case report of a serious adverse event following the administration of T cells transduced with a chimeric antigen receptor recognizing ERBB2," Mol Ther., 18(4):843-851.
Mullen et al., 1992, "Transfer of the bacterial gene for cytosine deaminase to mammalian cells confers lethal sensitivity to 5-fluorocytosine: a negative selection system," Proc Natl Acad Sci USA, 89(1):33-37.
Munshi et al., 2020, "Idecabtagene vicleucel (ide-cel; bb2121), a BCMA-targeted CAR T-cell therapy, in patients with relapsed and refractory multiple myeloma (RRMM): Initial KarMMa results," Journal of Clinical Oncology, 38(15):Abstract 8503.
Nakamura et al., 1986, "Purification and Characterization of a Growth Factor From Rat Platelets for Mature Parenchymal Hepatocytes in Primary Cultures," Proc Natl Acad Sci USA, 83(17):6489-6493.
Neri et al., 2007, "Neutralizing B-cell activating factor antibody improves survival and inhibits osteoclastogenesis in a severe combined immunodeficient human multiple myeloma model," Clin Cancer Res., 13(19):5903-5909.
Ng et al., 2004, "B cell-activating factor belonging to the TNF family (BAFF)-R is the principal BAFF receptor facilitating BAFF costimulation of circulating T and B cells," J Immunol., 173(2):807-817.
Novak et al., 2004, "Expression of BCMA, TACI, and BAFF-R in multiple myeloma: a mechanism for growth and survival," Blood, 103(2):689-694.
O'Connor et al., 2004, "BCMA is essential for the survival of long-lived bone marrow plasma cells," J Exp Med., 199(1):91-97.
Okutsu et al., 2014, "Cortisol is not the primary mediator for augmented CXCR4 expression on natural killer cells after acute exercise," J Appl Physiol, 117(3):199-204.
Orlandi et al., 1989, "Cloning immunoglobulin variable domains for expression by the polymerase chain reaction," Proc Natl Acad Sci USA, 86(10):3833-3837.
Pappa et al., 2014, "Prognostic impact of angiopoietin-2 in multiple myeloma," J Cancer Res Clin Oncol., 140(10):1801-1805.
Patel et al., 1999, "Impact of chimeric immune receptor extracellular protein domains on T cell function" Gene Ther., 6(3):412-419.
Pegram et al., 2014, "CD28z CARs and armored CARs," Cancer J., 20(2):127-133.
Perica et al., 2018, "Building a CAR Garage: Preparing for the Delivery of Commercial CAR T Cell Products at Memorial Sloan Kettering Cancer Center," Biol Blood Marrow Transplant, 24(6):1135-1141.
Pomerantz et al., 1995, "Structure-based design of transcription factors," Science, 267(5194):93-96.
Raje et al., 2019, "Anti-BCMA CAR T-Cell Therapy bb2121 in Relapsed or Refractory Multiple Myeloma," N Engl J Med., 380(18):1726-1737.
Reiners et al. 2013, "Rescue of impaired NK cell activity in hodgkin lymphoma with bispecific in antibodies vitro and in patients," Mol Ther., 21(4):895-903.
Reiss et al., 2001, "CC chemokine receptor (CCR)4 and the CCR10 ligand cutaneous T cell-attracting chemokine (CTACK) in lymphocyte trafficking to inflamed skin," J Exp Med., 194(10):1541-1547.
Riet, 2010, "Erhöhung der Antigen-Selektivität von T-Zellen durch Koexpression chimärer Antigen-Rezeptoren unterschiedlicher Spezifität," Ph.D. thesis, Dissertation Universitat zu Koln, retrieved from http://kups.ub.uni-koeln.de/3261, in German with English abstract only (204 pages).
Riet, 2010, "Increase of the antigen selectivity of T-cells by Koexpression of chimeric antigen receptors of divergent specificity," Ph.D. thesis, Dissertation Universitat zu Koln, machine English translation (204 pages).
Sadelain et al., 2013, "The basic principles of chimeric antigen receptor design," Cancer Discov., 3(4):388-398.
Sanchez et al., 2012, "Serum B-cell maturation antigen is elevated in multiple myeloma and correlates with disease status and survival," Br J Haematol, 158(6):727-738.
Schiemann et al., 2001, "An essential role for BAFF in the normal development of B cells through a BCMA-independent pathway," Science, 293(5537):2111-2114.
Shah et al., 2018, "Initial Results from a Phase 1 Clinical Study of bb21217, a Next-Generation Anti Bcma CAR T Therapy," Blood, 132:488 (6 pages).
Shah et al., 2020, "B-cell maturation antigen (BCMA) in multiple myeloma: rationale for targeting and current therapeutic approaches," Leukemia, 34(4):985-1005.
Sharp, 1999, "RNAi and double-strand RNA," Genes Dev., 13(2):139-141.
Shimabukuro-Vornhagen et al., 2018, "Cytokine release syndrome," J Immunother Cancer, 6(1):56 (14 pages).
Shiratori et al., 1999, "Strategy of liver-directed gene therapy: present status and future prospects," Liver, 19(4):265-274.
Sigmundsdottir et al., 2007, "DCs metabolize sunlight-induced vitamin D3 to 'program' T cell attraction to the epidermal chemokine CCL27," Nat Immunol., 8(3):285-293.
Singer et al., 2010, "Effective elimination of acute myeloid leukemic cells by recombinant bispecific antibody derivatives directed against CD33 and CD16," J Immunother., 33(6):599-608.
Somanchi et al., 2012, "Engineering lymph node homing of ex vivo-expanded human natural killer cells via trogocytosis of the chemokine receptor CCR7," Blood, 119(22):5164-5172.
Soneoka et al., 1995, "A transient three-plasmid expression system for the production of high titer retroviral vectors," Nucleic Acids Res., 23(4):628-633.
Song et al., 2013, "Chimeric NKG2D CAR-expressing T cell-mediated attack of human ovarian cancer is enhanced by histone deacetylase inhibition," Hum Gene Ther., 24(3):295-305.
Sonneveld et al., 2016, "Treatment of relapsed and refractory multiple myeloma," Haematologica, 101(4):396-406 and Errata Corrige published 101(8):995.
Southard et al., 1990, "Important components of the UW solution," Transplantation, 49(2):251-257.
Supplemental European Search Report of European Patent Application No. 14770151.0 completed Aug. 11, 2016 (1 page).
Szymczak et al., 2004, "Correction of multi-gene deficiency in vivo using a single 'self-cleaving' 2A peptide-based retroviral vector," Nat Biotechnol, 22(5):589-594 with Errata, Corrigenda and Addenda published Jun. 1, 2004 and Dec. 1, 2004.
Tang et al., 2010, "High-mobility group box 1 and cancer," Biochim Biophys Acta., 1799(1-2):131-140.
Terpos et al., 2012, "Circulating angiopoietin-1 to angiopoietin-2 ratio is an independent prognostic factor for survival in newly diagnosed patients with multiple myeloma who received therapy with novel antimyeloma agents," Int J Cancer, 130(3):735-742.
Tey et al., 2007, "Inducible caspase 9 suicide gene to improve the safety of allodepleted T cells after haploidentical stem cell transplantation," Biol. Blood Marrow Transplant., 13(8):913-924.
The Human Protein Atlas, Gene Name: CLEC12A, C-type lectin domain family 12 member A, retrieved from internet: http://www.proteinatlas.org/ENSG00000172322-CLEC12A/pathology, on Jan. 28, 2020 (2 pages).
Thomis et al., 2001, "A Fas-based suicide switch in human T cells for the treatment of graft-versus-host disease," Blood, 97(5):1249-1257.
Thompson et al., 2000, "BAFF binds to the tumor necrosis factor receptor-like molecule B cell maturation antigen and is important for maintaining the peripheral B cell population," J Exp Med., 192(1):129-135.

(56) References Cited

OTHER PUBLICATIONS

Thule et a l., 2000, "Regulated hepatic insulin gene therapy of STZ-diabetic rats," Gene Ther., 7(20):1744-1752.
Tsuji et al., 2003, "Concurrent induction of T-cell activation and apoptosis of osteosarcoma cells by adenovirus-mediated B7-1/Fas chimeric gene transfer", Cancer Gene Ther., 10(9):717-725.
UniProtKB—Q03267 (IKZF1_MOUSE), DNA-binding protein Ikaros, retrieved from https://www.uniprot.org/uniprot/Q03267-1 on Aug. 9, 2019, Integrated into UniProtKB/Swiss-Prot on Oct. 1, 1993, Last sequence update Dec. 15, 1998.
UniProtKB—Q96SW2 (CRBN_HUMAN), Protein cereblon, retrieved from https://www.uniprot.org/uniprot/Q96SW2 on Aug. 9, 2019, Integrated into UniProtKB/Swiss-Prot on Aug. 30, 2005, Last sequence update Dec. 1, 2001.
UniProtKB—Q9UKT9 (IKZF3_HUMAN), Zinc finger protein Aiolos, retrieved from https://www.uniprot.org/uniprot/Q9UKT9 on Aug. 9, 2019, Integrated into UniProtKB/Swiss-Prot on Sep. 19, 2002, Last sequence update Nov. 4, 2008.
Vallera et al., 2013, "Heterodimeric bispecific single-chain variable-fragment antibodies against EpCAM and CD16 induce effective antibody-dependent cellular cytotoxicity against human carcinoma cells," Cancer Biother Radiopharm., 28(4):274-282.
Wang et al., 2003, "Synthesis and characterization of a novel degradable phosphate-containing hydrogel," Biomaterials, 24(22):3969-3980.
Wang et al., 2016, "Clinical manufacturing of CAR T cells: foundation of a promising therapy," Mol Ther Oncolytics, 3:16015 (7 pages).
Ware et al., 1976, "Reanalysis of some baboon descent data," Biometrics, 32(2):459-463.
Wiernik et al., 2013, "Targeting natural killer cells to acute myeloid leukemia in vitro with a CD16×33 bispecific killer cell engager and ADAM17 inhibition," Clin Cancer Res., 19(14):3844-3855.
Wigler et al., 1977, "Transfer of purified herpes virus thymidine kinase gene to cultured mouse cells," Cell, 11(1):223-232.
Wikipedia, B-cell maturation antigen (BCMA) definition/description, 2017.
Wilkie et al., 2010, "Selective expansion of chimeric antigen receptor-targeted T-cells with potent effector function using interleukin-4," J Biol Chem., 285(33):25538-25544.
Wilkie et al., 2012, "Dual targeting of ErbB2 and MUC1 in breast cancer using chimeric antigen receptors engineered to provide complementary signaling," J Clin Immunol. 32(5):1059-1070.
Written Opinion of International Patent Application No. PCT/US2014/027039 (Pub No. WO2014152177) dated Jul. 7, 2014 (14 pages).
Wu et al., 1970, "An analysis of the sequences of the variable regions of Bence Jones proteins and myeloma light chains and their implications for antibody complementarity," J Exp Med., 132(2):211-250.
Wu et al., 2015, "Remote control of therapeutic T cells through a small molecule-gated chimeric receptor," Science, 350(6258):aab4077 (11 pages).
Xu et al., 2001, "B-cell maturation protein, which binds the tumor necrosis factor family members BAFF and APRIL, is dispensable for humoral immune responses," Mol Cell Biol., 21(12):4067-4074.
Yang et al., 1986, "A common pathway for T lymphocyte activation involving both the CD3-Ti complex and CD2 sheep erythrocyte receptor determinants," J Immunol, 137(4):1097-1100.
Yoshie, 2013, "Chemokine receptors as therapeutic targets," Jpn. J. Clini. Immunol., 36(4):189-196 (in Japanese with English Abstract).
Yssel et al., 1984, "Serum-free medium for generation and propagation of functional human cytotoxic and helper T cell clones," J Immunol Methods., 72(1):219-227.
Zamore et al., 2000, "RNAi: double-stranded RNA directs the ATP-dependent cleavage of mRNA at 21 to 23 nucleotide intervals," Cell, 101(1):25-33.
Zennou et al., 2000, "HIV-1 genome nuclear import is mediated by a central DNA flap," Cell, 101(2):173-185.
Zhan et al., 2001, "Insulator: from chromatin domain boundary to gene regulation," Hum Genet, 109(5):471-478.
Zufferey et al., 1999, "Woodchuck hepatitis virus post-transcriptional regulatory element enhances expression of transgenes delivered by retroviral vectors," J Virol., 73(4):2886-2892.
Requirement for Species Election dated Jun. 24, 2016 for U.S. Appl. No. 14/653,650 (6 pages).
Response to Requirement for Species Election filed Aug. 22, 2016 for U.S. Appl. No. 14/653,650 (6 pages).
Non-Final Office Action with List of References dated Sep. 16, 2016 for U.S. Appl. No. 14/653,650 (21 pages).
Response to Non-Final Office Action filed Feb. 22, 2017 for U.S. Appl. No. 14/653,650 (12 pages).
Final Office Action with List of References dated May 4, 2017 for U.S. Appl. No. 14/653,650 (16 pages).
Response to Final Office Action filed Nov. 3, 2017 for U.S. Appl. No. 14/653,650 (9 pages).
Non-Final Office Action with List of References dated Dec. 18, 2017 for U.S. Appl. No. 14/653,650 (10 pages).
Response to Non-Final Office Action filed Jun. 15, 2018 for U.S. Appl. No. 14/653,650 (14 pages).
Notice of Allowance with Examiner's Comments dated Jul. 31, 2018 for U.S. Appl. No. 14/653,650 (9 pages).
Requirement for Species Election dated Sep. 2, 2016 for U.S. Appl. No. 14/765,896 (11 pages).
Response to Requirement for Species Election filed Jan. 27, 2017 for U.S. Appl. No. 14/765,896 (2 pages).
Non-Final Office Action with List of References dated Apr. 27, 2017 for U.S. Appl. No. 14/765,896 (21 pages).
Response to Non-Final Office Action filed Oct. 26, 2017 for U.S. Appl. No. 14/765,896 (12 pages).
Final Office Action with List of References dated Nov. 29, 2017 for U.S. Appl. No. 14/765,896 (24 pages).
Non-Final Office Action with List of References dated Jun. 20, 2019 for U.S. Appl. No. 15/990,561 (19 pages).
Response to Non-Final Office Action filed Dec. 19, 2019 for U.S. Appl. No. 15/990,561 (14 pages).
Final Office Action dated Jan. 3, 2020 for U.S. Appl. No. 15/990,561 (19 pages).
Response to Non-Final Office Action filed Jul. 2, 2020 for U.S. Appl. No. 15/990,561 (18 pages).
Non-Final Office Action dated Oct. 16, 2020 for U.S. Appl. No. 15/990,561 (20 pages).
Requirement for Restriction and Species Election dated Dec. 21, 2016 for U.S. Appl. No. 14/775,891 (9 pages).
Response to Requirement for Restriction and Species Election filed Feb. 13, 2017 for U.S. Appl. No. 14/775,891 (8 pages).
Non-Final Office Action with List of References dated Apr. 25, 2017 for U.S. Appl. No. 14/775,891 (18 pages).
Response to Non-Final Office Action filed Oct. 24, 2017 for U.S. Appl. No. 14/775,891 (10 pages).
Notice of Allowance with Examiner's Amendment and Examiner Initiated Interview Summary dated Jan. 25, 2018 for U.S. Appl. No. 14/775,891 (9 pages).
Notice of Allowance with Examiner's Comment dated May 21, 2018 for U.S. Appl. No. 14/775,891 (9 pages).
Notice of Allowance with Examiner's Comment dated Nov. 20, 2018 for U.S. Appl. No. 14/775,891 (9 pages).
Notice of Allowance with Examiner's Comment and with List of References dated Aug. 14, 2020 for U.S. Appl. No. 16/276,581 (9 pages).
Notice of Allowance with Examiner's Comment dated Dec. 7, 2020 for U.S. Appl. No. 16/276,581 (7 pages).
Requirement for Restriction and Species Election with List of References dated Nov. 19, 2019 for U.S. Appl. No. 15/502,752 (8 pages).
Non-Final Office Action dated Apr. 1, 2020 for U.S. Appl. No. 15/502,752 (10 pages).
Requirement for Restriction and Species Election dated Dec. 27, 2018 for U.S. Appl. No. 15/541,006 (8 pages).
Response to Requirement for Restriction and Species Election filed Apr. 29, 2019 for U.S. Appl. No. 15/541,006 (9 pages).

(56) References Cited

OTHER PUBLICATIONS

Non-Final Office Action with List of References dated Aug. 19, 2019 for U.S. Appl. No. 15/541,006 (13 pages).
Bergeron et al., 1996, "MAUB is a new mucin antigen associated with bladder cancer," J. Biol. Chem., 271(12):6933-6940.
Buckner et al., 2007, "An unusual cause of elevated serum total beta hCG," Ann. Clin. Lab Sci., 37(2): 186-191.
Cullen et al., 2010, "Granzymes in cancer and immunity," Cell Death Differ., 17(4):616-623.
Gansauge et al., 1996, "CAM 17.1—a new diagnostic marker in pancreatic cancer," Br. J. Cancer, 74(12):1997-2002.
Miotti et al., 1992, "Membrane association and shedding of the GPI-anchored Ca-MOv18 antigen in human ovary carcinoma cells," Int. J. Cancer, 51(3):499-505.
Rottiers et al., 1998, "Differentiation of EL4 lymphoma cells by tumoral environment is associated with inappropriate expression of the large chondroitin sulfate proteoglycan PG-M and the tumor-associated antigen Htgp-175," Int. J. Cancer, 78(4):503-510.
Teriukova et al., 2003, "Effect of narrow fractions of chromatin non-histone proteins on the expression of membrane tumor-associated antigen MA-50 and phosphorylation of proteins of cultured rat hepatocytes," Tsitologiia, 45(3):277-283 (in German with English Abstract).

\* cited by examiner

CHIMERIC ANTIGEN RECEPTORS

This application is a continuation of U.S. patent application Ser. No. 14/653,650, issued as U.S. Pat. No. 10,150,816, which is a U.S. national stage of International Patent Application No. PCT/US2013/076486, filed on Dec. 19, 2013, which claims the benefit of U.S. Provisional Patent Application No. 61/740,113, filed Dec. 20, 2012, and U.S. Provisional Patent Application No. 61/779,925, filed Mar. 13, 2013, the disclosure of each of which is incorporated by reference herein in its entirety.

SEQUENCE LISTING

A Sequence Listing in Computer Readable Form ("CRF"), which is an ASCII text file of 4,682 bytes in size entitled 12827-883-999_SEQ_LISTING.txt, created on Oct. 30, 2018, which is being filed concurrently with the instant application via EFS-Web, is incorporated by reference herein in its entirety.

1. FIELD

The disclosure herein relates to the field of immunology, and more specifically, to the modification of T lymphocytes or other immune cells.

2. BACKGROUND

Cells of the immune system such as T lymphocytes (also referred to as T cells) recognize and interact with specific antigens through receptors or receptor complexes which, upon recognition or an interaction with such antigens, cause activation of the cell. An example of such a receptor is the antigen-specific T lymphocyte receptor complex (TCR/CD3), a complex of eight proteins. The T cell receptor (TCR) is expressed on the surface of T lymphocytes. One component, CD3, which has an invariant structure, is responsible for intracellular signaling following occupancy of the TCR by ligand. The T lymphocyte receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T lymphocyte targets. Stimulation of the TCR/CD3 complex results in activation of the T lymphocyte and a consequent antigen-specific immune response. The TCR/CD3 complex plays a central role in the effector function and regulation of the immune system.

T lymphocytes require a second, co-stimulatory signal to become fully active. Without such a signal, T lymphocytes are either non-responsive to antigen binding to the TCR, or become anergic. Such a co-stimulatory signal, for example, is provided by CD28, a T lymphocyte protein, which interacts with CD80 and CD86 on antigen-producing cells. ICOS (Inducible COStimulator), another T lymphocyte protein, provides a co-stimulatory signal when bound to ICOS ligand. CTLA4 (cytotoxic T-Lymphocyte Antigen 4), also known as CD152, is a receptor expressed on the surface of helper T cells and CD4+ T cells, that downregulates T cell activity. Binding of CTLA4 to its cognate ligands, CD80 and CD86, results in reduced T cell activation and proliferation. PD-1 (Programmed Cell Death-1), also known as CD279, is currently understood to negatively regulate T Cell Receptor (TCR) signals, and to broadly negatively regulate immune responses.

The essential antigen-binding, signaling, and stimulatory functions of the TCR complex have been reduced by genetic recombination methods to a single polypeptide chain, generally referred to as a Chimeric Antigen Receptor (CAR). See, e.g., Eshhar, U.S. Pat. No. 7,741,465; Eshhar, U.S. Patent Application Publication No. 2012/0093842. T lymphocytes bearing such CARs are generally referred to as CAR-T lymphocytes. CARs are constructed specifically to stimulate T cell activation and proliferation in response to a specific antigen to which the CAR binds.

3. SUMMARY

In one aspect, provided herein are polypeptides, e.g., chimeric antigen receptors (see, e.g., Eshhar, U.S. Pat. No. 7,741,465), that can be expressed by immune system cells, e.g., T lymphocytes (T cells), are membrane-bound in such immune system cells, and which comprise a transmembrane domain from an immune system protein that normally transmits an inhibitory signal to such immune system cells, e.g., a transmembrane domain from CTLA4 (Cytotoxic T-Lymphocyte Antigen 4 or Cytotoxic T-Lymphocyte Associated protein 4) or PD-1 (Programmed Cell Death-1).

In one embodiment, provided herein is a polypeptide comprising (i) a transmembrane domain comprising the transmembrane domain from CTLA4 (e.g., GenBank Accession No. NM_005214.4 (CTLA4 cytotoxic T-lymphocyte-associated protein 4 (*Homo sapiens*); Gene ID: 1493)) or PD-1 (e.g., GenBank Accession No. NM_005018.2 (programmed cell death 1 (*Homo sapiens*); Gene ID: 5133)), or a portion thereof, (ii) an intracellular domain (e.g., cytoplasmic domain) of an endogenous protein expressed on the surface of lymphocytes that triggers the activation and/or proliferation of said lymphocytes, and (iii) an extracellular domain that binds to an antigen of interest, wherein if the transmembrane domain is from CTLA4, the intracellular domain and extracellular domain of said polypeptide are not from CTLA4; and if the transmembrane domain is from PD-1, the intracellular domain and extracellular domain of said polypeptide are not from PD-1. In a specific embodiment, the polypeptide is a chimeric antigen receptor (CAR). In a specific embodiment, a T lymphocyte expressing said polypeptide, or any of such polypeptides described herein, is activated or stimulated to proliferate when said polypeptide binds to said antigen. In a specific embodiment, the polypeptide, when expressed on the surface of a T lymphocyte, directs the T lymphocyte to kill a cell expressing said antigen.

In a specific embodiment, provided herein is a polypeptide comprising a transmembrane domain from CTLA4, wherein the CTLA4 transmembrane domain is the polypeptide sequence encoded by exon 3 of a human ctla4 gene (e.g., GenBank Accession No. NM_005214.4 (CTLA4 cytotoxic T-lymphocyte-associated protein 4 (*Homo sapiens*); Gene ID: 1493)).

In another specific embodiment, the CTLA4 transmembrane domain of a polypeptide provided herein is or comprises the amino acid sequence (SEQ ID NO: 1)
PEPCPDSDFLLWILAAVSSGLFFYSFLLTAVSLSKM (in three-letter code, Pro-Glu-Pro-Cys-Pro-Asp- Ser-Asp-Phe-Leu-Leu-Trp-Ile-Leu-Ala-Ala-Val-Ser- -continued Ser-Gly-Leu-Phe-Phe-Tyr-Ser-Phe-Leu-Leu-Thr-Ala-Val-Ser-Leu-Ser-Lys-Met).

In another specific embodiment, the CTLA4 transmembrane domain of a polypeptide provided herein is or comprises the polypeptide sequence encoded by nucleotides 610-722 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence (SEQ ID NO: 2)
PDSDFLLWILAAVSSGLFFYSFLLTAVSL (in three-letter code, Pro-Asp-Ser-Asp-Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val-Ser-Leu).

In another specific embodiment, the CTLA4 transmembrane domain of a polypeptide provided herein is or comprises the polypeptide sequence encoded by nucleotides 636-699 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence FLLWILAAVSSGLFFYSFLLTAV (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val) (SEQ ID NO:3).

In another specific embodiment, the CTLA4 transmembrane domain of a polypeptide provided herein is or comprises the polypeptide sequence FLLWILAAVSSGLFFYSFLLT (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr) (SEQ ID NO:4).

In another specific embodiment, the CTLA4 transmembrane domain of a polypeptide provided herein is or comprises the polypeptide sequence (SEQ ID NO: 5)
FLLWILVAVSLGLFFYSFLVSAVSLS (in three-letter code, Phe-Leu-Leu-Trp-Ile-Leu-Val-Ala-Val-Ser-Leu-Gly-Leu-Phe-Phe-Tyr-Ser-Phe-Leu-Val-Ser-Ala-Val-Ser-Leu-Ser).

In another specific embodiment, the CTLA4 transmembrane domain of a polypeptide provided herein is or comprises the polypeptide sequence (SEQ ID NO: 9)
LGIGNGTQIYVIDPEPSPDSDFLLWILAAVSSGLFFYSFLLTAVSLSKM (in three-letter code, Leu Gly Ile Gly Asn Gly Thr Gln Ile Tyr Val Ile Asp Pro Glu Pro Ser Pro Asp Ser Asp Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, the CTLA4 transmembrane domain of a polypeptide provided herein is or comprises the polypeptide sequence (SEQ ID NO: 10)
FLLWILAAVSSGLFFYSFLLTAVSLSKM (in three-letter code, Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, the PD-1 transmembrane domain of a polypeptide provided herein is or comprises the amino acid sequence (SEQ ID NO: 6)
TLVVGVVGGLLGSLVLLVWVLAVICSRAA (in three-letter code, Thr-Leu-Val-Val-Gly-Val-Val-Gly-Gly-Leu-Leu-Gly-Ser-Leu-Val-Leu-Leu-Val-Trp-Val-Leu-Ala-Val-Ile-Cys-Ser-Arg-Ala-Ala).

In another specific embodiment, the PD-1 transmembrane domain of a polypeptide provided herein is or comprises the amino acid sequence VGVVGGLLGSLVLLVWVLAVI (in three-letter code, Val-Gly-Val-Val-Gly-Gly-Leu-Leu-Gly-Ser-Leu-Val-Leu-Leu-Val-Trp-Val-Leu-Ala-Val-Ile) (SEQ ID NO:7).

In another specific embodiment, the PD-1 transmembrane domain of a polypeptide provided herein is or comprises the amino acid sequence (SEQ ID NO: 8)
FQTLVVGVVGGLLGSLVLLVWVLAVI (in three-letter code, Phe-Gln-Thr-Leu-Val-Val-Gly-Val-Val-Gly-Gly-Leu-Leu-Gly-Ser-Leu-Val-Leu-Leu-Val-Trp-Val-Leu-Ala-Val-Ile).

In another specific embodiment, the PD-1 transmembrane domain of a polypeptide provided herein is or comprises the amino acid sequence (SEQ ID NO: 11)
FQTLVVGVVGGLLGSLVLLVWVLAVICSRAA (in three-letter code, Phe Gln Thr Leu Val Val Gly Val Val Gly Gly Leu Leu Gly Ser Leu Val Leu Leu Val Trp Val Leu Ala Val Ile Cys Ser Arg Ala Ala).

As exemplified by the CTLA-4 and PD-1 transmembrane domain sequences described herein (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11), the transmembrane domains described herein, in certain embodiments, comprise one or more amino acids from the extracellular domain and/or one or more amino acids from the intracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1). In certain embodiments, the transmembrane domains described herein comprise (i) 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1) and (ii) 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1).

In another specific embodiment, provided herein is a polypeptide that comprises a transmembrane domain, wherein the transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a polypeptide that comprises a transmembrane domain, wherein the transmembrane domain is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, the polypeptides provided herein comprise 1, 2, 3, 4, or 5 amino mutations, e.g., conservative amino acid mutations (e.g., hydrophobic amino acid mutated to a different hydrophobic amino acid), in the transmembrane domain of the polypeptide.

In certain embodiments, provided herein is a nucleotide sequence that encodes one of the polypeptides disclosed herein. In a specific embodiment, provided herein is a nucleotide sequence that comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid that encodes a polypeptide described herein, wherein the nucleic acid comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid sequence that encodes a polypeptide that is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In certain embodiments, the extracellular domain of any of the polypeptides described herein comprises a receptor, or a portion of a receptor, that binds to an antigen. The extracellular domain may be, e.g., a receptor, or a portion of a receptor, that binds to said antigen. In certain embodiments, the extracellular domain comprises, or is, an antibody or an antigen-binding portion thereof. In a specific embodiment, the extracellular domain comprises, or is, a single-chain Fv domain. The single-chain Fv domain can comprise, for example, a $V_L$ linked to $V_H$ by a flexible linker, wherein said $V_L$ and $V_H$ are from an antibody that binds said antigen.

The antigen to which the extracellular domain of the polypeptide binds can be any antigen of interest, e.g., an antigen on a tumor cell. The tumor cell may be, e.g., a cell in a solid tumor, or a cell of non-solid tumor, e.g., a cell of a blood cancer. In certain embodiments, the antigen is a tumor-associated antigen or a tumor-specific antigen. In a specific embodiment, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein. In another specific embodiment, said tumor-associated antigen or tumor-specific antigen is integrin $\alpha v \beta 3$ (CD61), galactin, K-Ras (V-Ki-ras2 Kirsten rat sarcoma viral oncogene), or Ral-B.

In certain embodiments, the extracellular domain of the polypeptides described herein is joined to the transmembrane domain of the polypeptide by a linker, spacer or hinge polypeptide/peptide sequence, e.g., a CH2CH3 hinge sequence or a sequence from CD8, CD28, CTLA4, or PD-1.

In certain embodiments, the intracellular domain of the polypeptides described herein is or comprises an intracellular domain of a protein that is expressed on the surface of T cells and triggers activation and/or proliferation of said T cells. In a specific embodiment, the intracellular domain is a CD3ζ intracellular signaling domain. In another specific embodiment, the intracellular domain is from a lymphocyte receptor chain, a TCR/CD3 complex protein, an Fc receptor subunit, or an IL-2 receptor subunit.

In certain embodiments, the polypeptides provided herein additionally comprise one or more co-stimulatory domains, e.g., as part of the intracellular domain of the polypeptide. The one or more co-stimulatory domains can be, or can comprise, without limitation, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or, a co-stimulatory inducible T-cell costimulatory (ICOS) polypeptide sequence.

In a specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 or CTLA4 hinge polypeptide sequence; (iii) a CTLA4 or PD-1 transmembrane domain; (iv) a costimulatory domain; and (v) an intracellular signaling domain. In a specific embodiment, the antigen-binding domain of the polypeptide binds to CD19.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 hinge polypeptide sequence; (iii) a CTLA4 or PD-1 transmembrane domain; (iv) a 4-1BB costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a PD-1 transmembrane domain; (iv) a CD28 costimulatory domain; and (v) a CD3ζ intracellular signaling domain.

In another aspect, provided herein are T lymphocytes, e.g., T cells, that comprise, e.g., express on their cell surface, a membrane-bound polypeptide, wherein said polypeptide comprises (i) a transmembrane domain comprising the transmembrane domain from CTLA4 or PD-1, or a portion thereof, (ii) an intracellular domain of an endogenous protein expressed on the surface of lymphocytes and that triggers the activation and/or proliferation of said lymphocytes, and (iii) an extracellular domain that binds to an antigen of interest, wherein if the transmembrane domain is from CTLA4, the intracellular domain and extracellular domain (optionally excluding a CTLA4 linker) of said polypeptide are not from CTLA4; and if the transmembrane domain is from PD-1, the intracellular domain and extracellular domain of said polypeptide are not from PD-1. In a specific embodiment, the polypeptide is a chimeric antigen receptor (CAR).

In a specific embodiment, provided herein is a T lymphocyte comprising a polypeptide that comprises a transmembrane domain from CTLA4, wherein the CTLA4 transmembrane domain is the polypeptide sequence encoded by exon 3 of a human CTLA4 gene (e.g., GenBank Accession No. NM_005214.4 (CTLA4 cytotoxic T-lymphocyte-associated protein 4 (*Homo sapiens*); Gene ID: 1493)).

In another specific embodiment, provided herein is a T lymphocyte comprising a polypeptide that comprises a transmembrane domain from CTLA4, wherein the CTLA4 transmembrane domain is or comprises the amino acid sequence

```
                                        (SEQ ID NO: 1)
PEPCPDSDFLLWILAAVSSGLFFYSFLLTAVSLSKM (in three-letter code, Pro-Glu-Pro-Cys-Pro-Asp- Ser-Asp-Phe-Leu-Leu-Trp-Ile-Leu-Ala-Ala-Val-Ser- Ser-Gly-Leu-Phe-Phe-Tyr-Ser-Phe-Leu-Leu-Thr-Ala- Val-Ser-Leu-Ser-Lys-Met).
```

In another specific embodiment, provided herein is a T lymphocyte comprising a polypeptide that comprises a transmembrane domain from CTLA4, wherein the CTLA4 transmembrane domain is or comprises the polypeptide sequence encoded by nucleotides 610-722 of GenBank Accession No. NM_005214.4 (CTLA4 cytotoxic T-lymphocyte-associated protein 4 (*Homo sapiens*); Gene ID: 1493).

In another specific embodiment, provided herein is a T lymphocyte comprising a polypeptide that comprises a transmembrane domain from CTLA4, wherein the CTLA4 transmembrane domain is or comprises the amino acid sequence

```
                                                      (SEQ ID NO: 2)
PDSDFLLWILAAVSSGLFFYSFLLTAVSL (in three-letter code, Pro-Asp-Ser-Asp-Phe-Leu- Leu-Trp-Ile-Leu-Ala-Ala-Val-Ser-Ser-Gly-Leu-Phe- Phe-Tyr-Ser-Phe-Leu-Leu-Thr-Ala-Val-Ser-Leu).
```

In another specific embodiment, provided herein is a T lymphocyte comprising a polypeptide that comprises a transmembrane domain from CTLA4, wherein the CTLA4 transmembrane domain is or comprises the polypeptide sequence encoded by nucleotides 636-699 of GenBank Accession No. NM_005214.4 (CTLA4 cytotoxic T-lymphocyte-associated protein 4 (*Homo sapiens*); Gene ID: 1493).

In another specific embodiment, provided herein is a T lymphocyte comprising a polypeptide that comprises a transmembrane domain from CTLA4, wherein the CTLA4 transmembrane domain is or comprises the amino acid sequence

```
                                                      (SEQ ID NO: 3)
FLLWILAAVSSGLFFYSFLLTAV (in three-letter code, Phe-Leu-Leu-Trp-Ile-Leu- Ala-Ala-Val-Ser-Ser-Gly-Leu-Phe-Phe-Tyr-Ser-Phe- Leu-Leu-Thr-Ala-Val).
```

In another specific embodiment, provided herein is a T lymphocyte comprising a polypeptide that comprises a transmembrane domain from CTLA4, wherein the CTLA4 transmembrane domain is or comprises the polypeptide sequence

```
                                                      (SEQ ID NO: 4)
FLLWILAAVSSGLFFYSFLLT (in three-letter code, Phe-Leu-Leu-Trp-Ile-Leu- Ala-Ala-Val-Ser-Ser-Gly-Leu-Phe-Phe-Tyr-Ser-Phe- Leu-Leu-Thr).
```

In another specific embodiment, provided herein is a T lymphocyte comprising a polypeptide that comprises a transmembrane domain from CTLA4, wherein the CTLA4 transmembrane domain is or comprises the polypeptide sequence

```
                                                  (SEQ ID NO: 5)
FLLWILVAVSLGLFFYSFLVSAVSLS (in three-letter code, Phe-Leu-Leu-Trp-Ile-Leu-Val-Ala-Val-Ser-Leu-Gly- Leu-Phe-Phe-Tyr-Ser-Phe-Leu-Val-Ser-Ala-Val-Ser- Leu-Ser).
```

In another specific embodiment, provided herein is a T lymphocyte comprising a polypeptide that comprises a transmembrane domain from CTLA4, wherein the CTLA4 transmembrane domain is or comprises the polypeptide sequence

```
                                                      (SEQ ID NO: 9)
LGIGNGTQIYVIDPEPSPDSDFLLWILAAVSSGLFFYSFLLTAVSLSKM (in three-letter code, Leu Gly Ile Gly Asn Gly Thr Gln Ile Tyr Val Ile Asp Pro Glu Pro Ser Pro Asp Ser Asp Phe Leu Leu Trp Ile Leu Ala Ala Val Ser Ser Gly Leu Phe Phe Tyr Ser Phe Leu Leu Thr Ala Val Ser Leu Ser Lys Met).
```

In another specific embodiment, provided herein is a T lymphocyte comprising a polypeptide that comprises a transmembrane domain from CTLA4, wherein the CTLA4 transmembrane domain is or comprises the polypeptide sequence

```
                                                     (SEQ ID NO: 10)
FLLWILAAVSSGLFFYSFLLTAVSLSKM (in three-letter code, Phe Leu Leu Trp Ile Leu Ala Ala Val Ser Ser Gly Leu Phe Phe Tyr Ser Phe Leu Leu Thr Ala Val Ser Leu Ser Lys Met).
```

In another specific embodiment, provided herein is a T lymphocyte comprising a polypeptide that comprises a transmembrane domain from PD-1, wherein the PD-1 transmembrane domain is or comprises the amino acid sequence

```
                                                      (SEQ ID NO: 6)
TLVVGVVGGLLGSLVLLVWVLAVICSRAA (in three-letter code, Thr-Leu-Val-Val-Gly-Val-Val-Gly-Gly-Leu- Leu-Gly-Ser-Leu-Val-Leu-Leu-Val-Trp-Val-Leu-Ala- Val-Ile-Cys-Ser-Arg-Ala-Ala).
```

In another specific embodiment, provided herein is a T lymphocyte comprising a polypeptide that comprises a transmembrane domain from PD-1, wherein the PD-1 transmembrane domain is or comprises the amino acid sequence

```
                                                      (SEQ ID NO: 7)
VGVVGGLLGSLVLLVWVLAVI (in three-letter code, Val- Gly-Val-Val-Gly-Gly-Leu-Leu-Gly-Ser-Leu-Val-Leu- Leu-Val-Trp-Val-Leu-Ala-Val-Ile).
```

In another specific embodiment, provided herein is a T lymphocyte comprising a polypeptide that comprises a transmembrane domain from PD-1, wherein the PD-1 transmembrane domain is or comprises the amino acid sequence

```
                                                      (SEQ ID NO: 8)
FQTLVVGVVGGLLGSLVLLVWVLAVI (in three-letter code, Phe-Glu-Thr-Leu-Val-Val-Gly-Val-Val-Gly-Gly-Leu- Leu-Gly-Ser-Leu-Val-Leu-Leu-Val-Trp-Val-Leu-Ala- Val-Ile).
```

In another specific embodiment, provided herein is a T lymphocyte comprising a polypeptide that comprises a transmembrane domain from PD-1, wherein the PD-1 transmembrane domain is or comprises the amino acid sequence (SEQ ID NO: 11)
FQTLVVGVVGGLLGSLVLLVWVLAVICSRAA (in three-letter code, Phe Gln Thr Leu Val Val Gly Val Val Gly Gly Leu Leu Gly Ser Leu Val Leu Val Trp Val Leu Ala Val Ile Cys Ser Arg Ala Ala).

In certain embodiments, a nucleotide sequence expressed or encoded by a T lymphocyte provided herein (i.e., a T lymphocyte comprising a polypeptide described herein) comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In another specific embodiment, provided herein is a T lymphocyte comprising a polypeptide that comprises a transmembrane domain, wherein the transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In certain embodiments, provided herein is a T lymphocyte comprising a nucleic acid that encodes a polypeptide described herein, wherein the nucleic acid comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In certain embodiments, the extracellular domain of a polypeptide expressed by the T lymphocytes provided herein comprises a receptor, or a portion of a receptor, that binds to an antigen of interest. The extracellular domain may be, e.g., a receptor, or a portion of a receptor, that binds to said antigen. In certain embodiments, the extracellular domain comprises, or is, an antibody or an antigen-binding portion thereof. In specific embodiments, the extracellular domain comprises, or is, a single-chain Fv domain. The single-chain Fv domain can comprise, for example, a $V_L$ linked to $V_H$ by a flexible linker, wherein said $V_L$ and $V_H$ are from an antibody that binds said antigen.

The antigen to which the extracellular domain of the polypeptide expressed by a T lymphocyte provided herein binds, and therefore to which the T cell is directed by the polypeptide, can be any antigen of interest, e.g., an antigen on a tumor cell. The tumor cell may be, e.g., a cell in a solid tumor, or a cell of a non-solid tumor, e.g., a cell of a blood cancer. In certain embodiments, the antigen is a tumor-associated antigen or a tumor-specific antigen. In certain embodiments, the antigen is one or more of Kappa, Lambda, CD19, CD22, CD27, CD30, CD70, GD2, HER2, CEA, EGFRvIII, Sperm Protein17, PSCA, mesothelin, PAP (prostatic acid phosphatase), prostein, TARP (T cell receptor gamma alternate reading frame protein), Trp-p8, STEAP1 (six-transmembrane epithelial antigen of the prostate 1), and/or MUC-1. In various specific embodiments, without limitation, the tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In another specific embodiment, said tumor-associated antigen or tumor-specific antigen is integrin αvβ3 (CD61), galactin, K-Ras (V-Ki-ras2 Kirsten rat sarcoma viral oncogene), or Ral-B.

In certain embodiments, the extracellular domain of a polypeptide expressed by a T lymphocyte described herein is joined to said transmembrane domain of the polypeptide by a linker, spacer or hinge polypeptide sequence, e.g., a sequence from CD8, CD28, CTLA4 or PD-1.

In certain embodiments, the intracellular domain of a polypeptide expressed by a T lymphocyte described herein is or comprises an intracellular domain of a protein that is normally expressed on the surface of T cells and which triggers activation and/or proliferation of said T cells. In a specific embodiment, the intracellular domain is a CD3ζ intracellular signaling domain. In another embodiment, the intracellular domain is from a lymphocyte receptor chain, a TCR/CD3 complex protein, an Fc receptor subunit or an IL-2 receptor subunit.

In certain embodiments, a polypeptide expressed by a T lymphocyte described herein additionally comprises one or more co-stimulatory domains, e.g., as part of the intracellular domain of the polypeptide. The one or more co-stimulatory domains can be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence.

In a specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a CD28 or CTLA4 hinge polypeptide sequence; (iii) a CTLA4 or PD-1 transmembrane domain; (iv) a costimulatory domain; and (v) an intracellular signaling domain. In a specific embodiment, the antigen-binding domain of the polypeptide binds to CD19.

In a specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain. In a specific embodiment, the antigen-binding domain of the polypeptide binds to HER2.

In a specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain. In a specific embodiment, the antigen-binding domain of the polypeptide binds to HER2.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a CTLA4 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a CD28 costimulatory domain; and (v) a CD3ζ intracellular signaling domain.

In another specific embodiment, the T lymphocytes provided herein express or comprise a polypeptide that comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a PD-1 transmembrane domain; (iv) a CD28 costimulatory domain; and (v) a CD3ζ intracellular signaling domain.

In a specific embodiment, the T lymphocytes provided herein that express or comprise one or more of the polypeptides provided herein, become activated or stimulated to proliferate when said polypeptide binds to the antigen to which the antigen binding domain or single-chain Fv domain of the polypeptide is specific. In another specific embodiment, the T lymphocytes provided herein that express or comprise one or more of the polypeptides provided herein, kill cells that express or comprise the antigen to which the antigen binding domain or single-chain Fv domain of the polypeptide is specific when the T lymphocytes come in contact with said antigen-expressing cells.

In another aspect, provided herein are methods of treating an individual having a disease or disorder, wherein the disease or disorder is characterized, or is characterizable, by cells expressing an antigen, comprising administering to the individual one or more of the T lymphocytes provided herein, i.e., T lymphocytes that comprise or express a polypeptide described herein.

4. BRIEF DESCRIPTION OF THE DRAWINGS

Figure 6A:
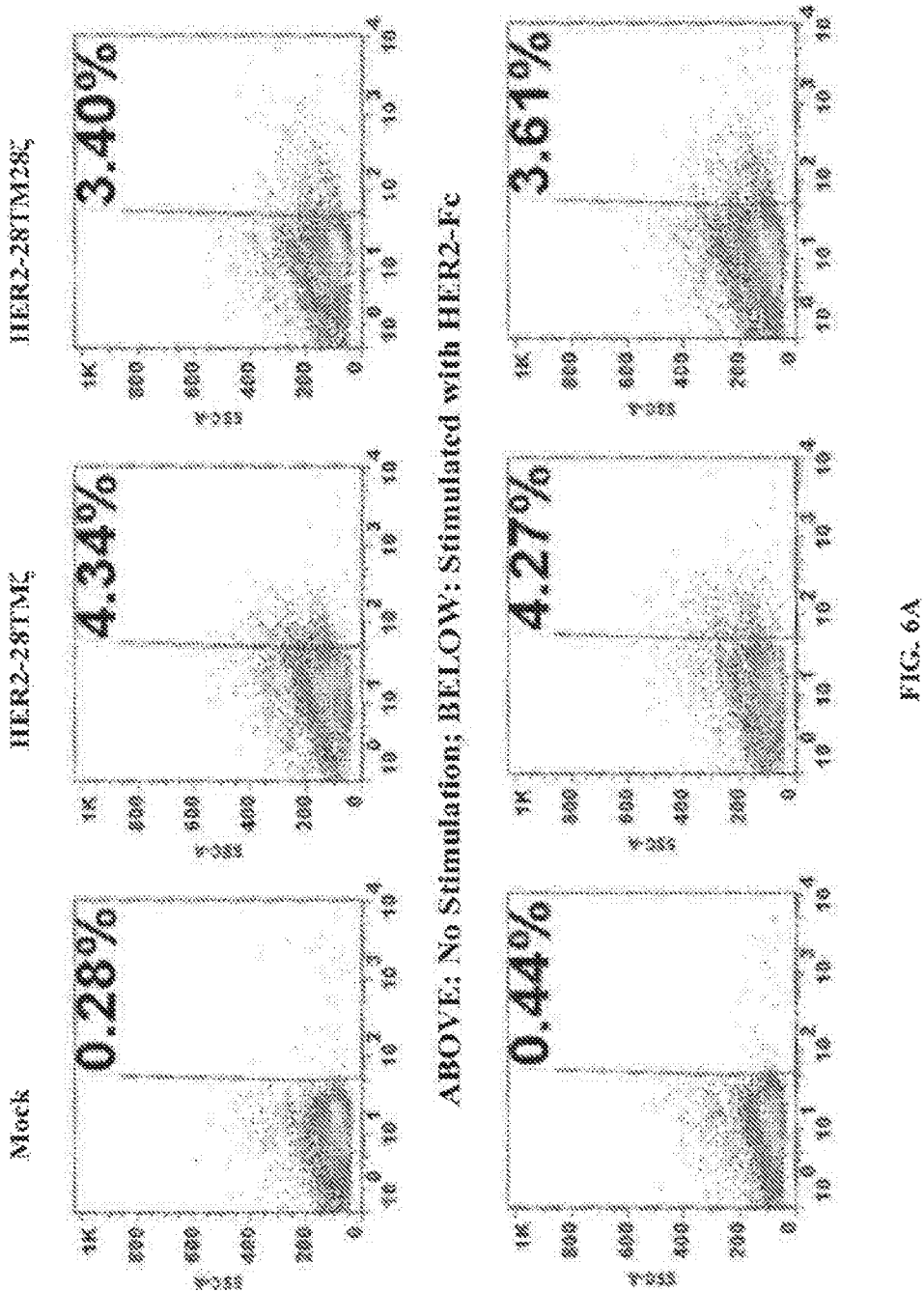
Figure 6B:
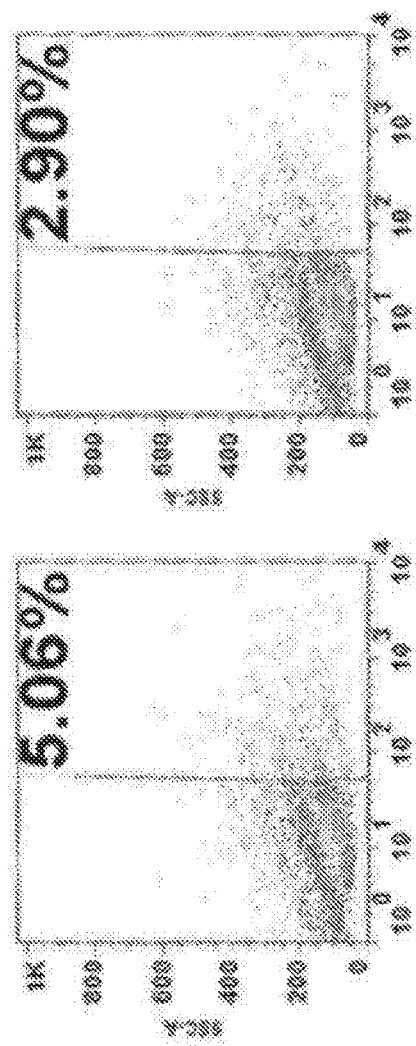
Figure 6B:
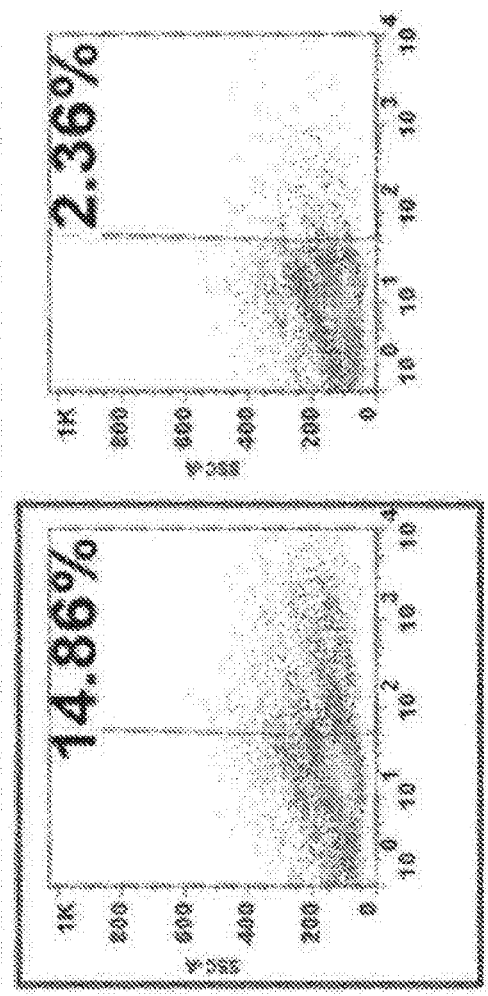

FIGS. 6A-6B depict percentages of CAR T cells the express certain anti-HER2 CARs or a mock control in the absence (top panels) and presence (bottom panels) of stimulation with HER2-Fc. FIG. 6A) Percentages of anti-HER2 CAR T cells expressing Mock, HER2-28TMζ, or HER2-28TM28ζ. FIG. 6B) Percentages of anti-HER2 CAR T cells expressing HER2-CTLA4TM28ζ or HER2-4-1BBTM28ζ.

Figure 7:
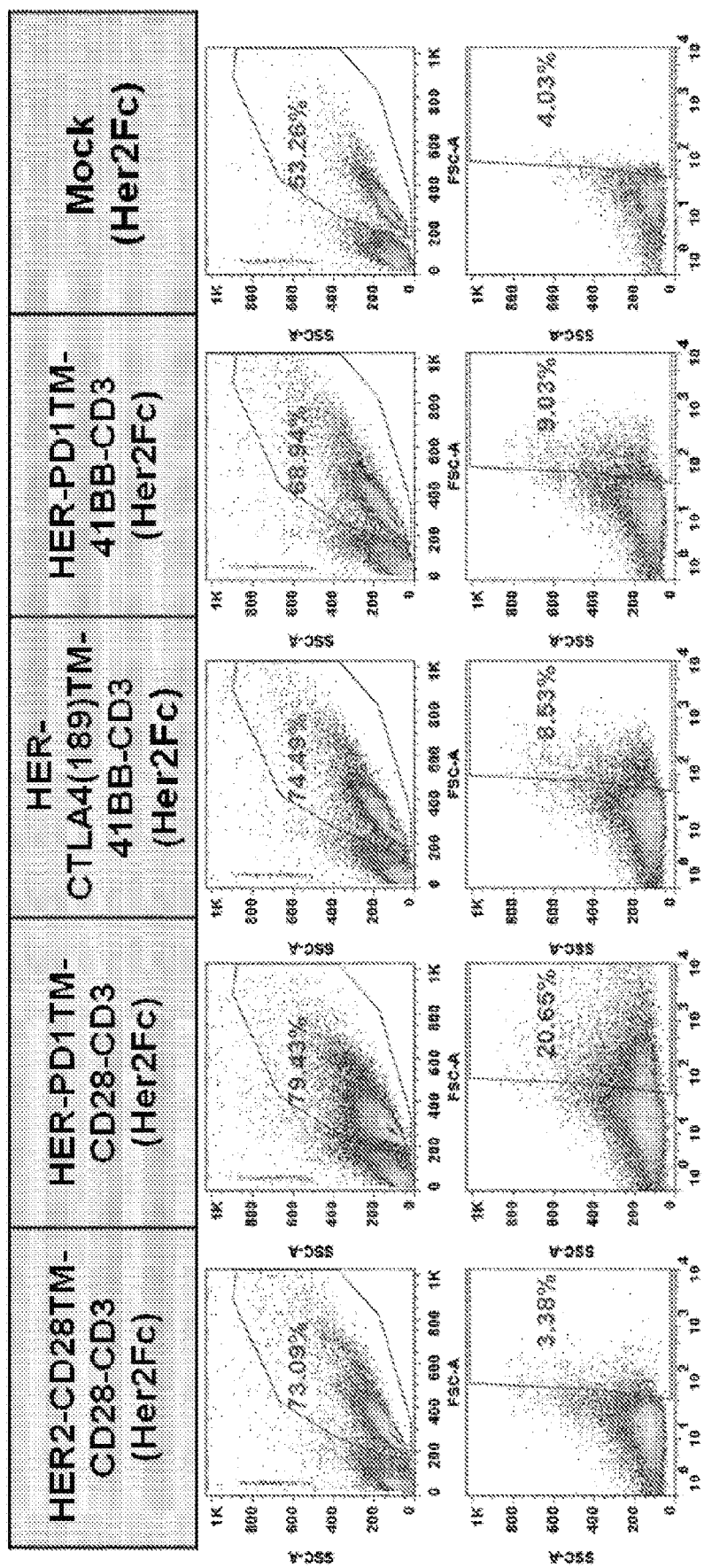

FIG. 7 depicts expression of CARs by T cells eleven days after transduction of the T cells with lentiviral vectors that express the CARS.

Figure 8:
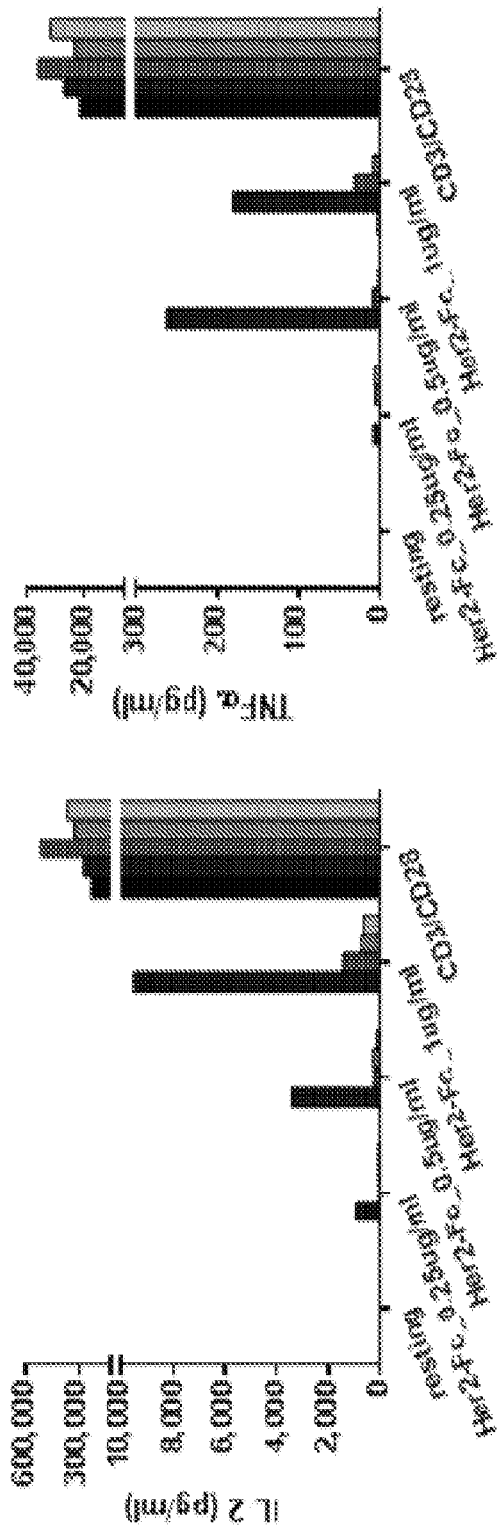

FIG. 8 depicts IL-2, TNF-α, and IFN-γ production by CAR T cells (i) in the resting state, (ii) after exposure to 0.25, 0.5, or 1.0 μg/ml HER2-Fc; or (iii) after CD3/CD28 ligation. First (leftmost) bar in each group: mock-transduced cells (no CAR expressed); second bar in each group: cells transduced with CAR designated HER-PD1TM-CD28-CD3; third bar in each group: cells transduced with CAR designated HER-CTLA4(189)TM-41BB-CD3; fourth bar in each group: cells transduced with CAR designated HER- PD1TM-41BB-CD3; fifth (rightmost) bar in each group: cells transduced with CAR designated HER2-CD28TM-CD28-CD3.

Figure 9:
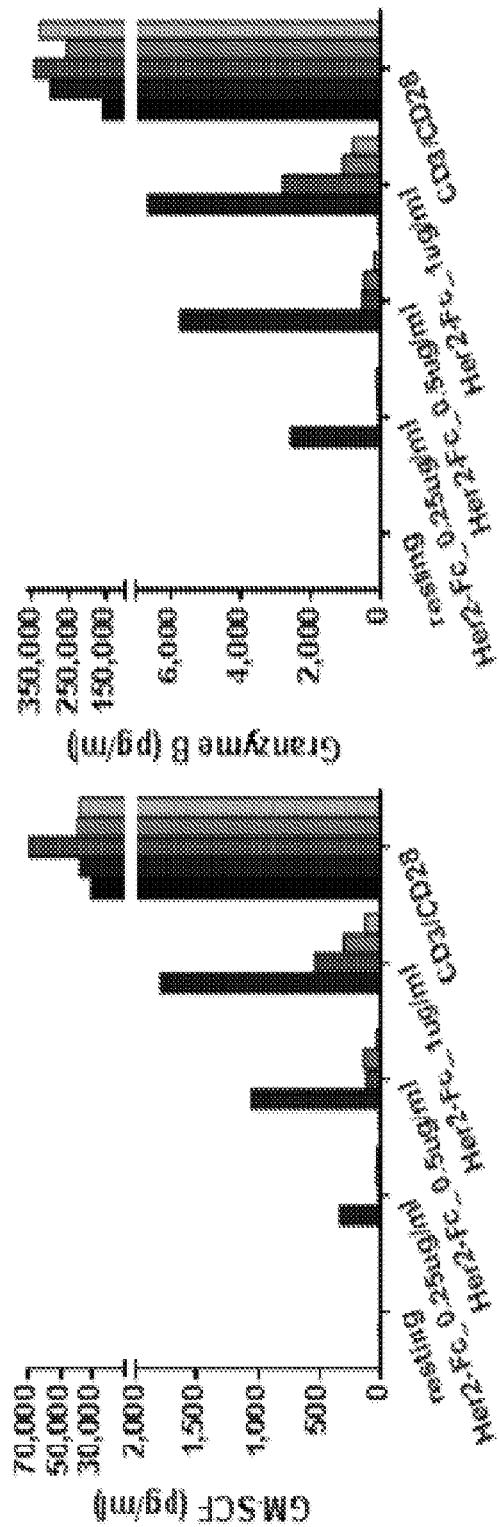
Figure 9:
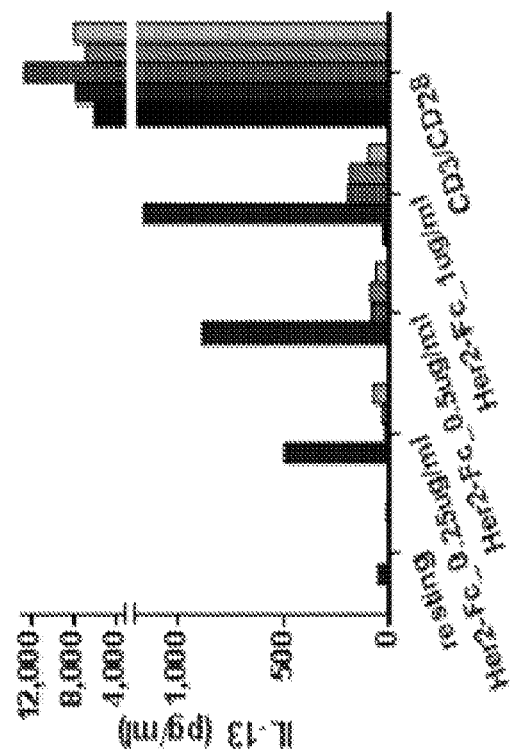

FIG. 9 depicts GM-CSF, Granzyme B, and IL-13 production by CAR T cells (i) in the resting state, (ii) after exposure to 0.25, 0.5, or 1.0 µg/ml HER2-Fc; or (iii) after CD3/CD28 ligation. First (leftmost) bar in each group: mock-transduced cells (no CAR expressed); second bar in each group: cells transduced with CAR designated HER-PD1TM-CD28-CD3; third bar in each group: cells transduced with CAR designated HER-CTLA4(189)TM-41BB-CD3; fourth bar in each group: cells transduced with CAR designated HER-PD1TM-41BB-CD3; fifth (rightmost) bar in each group: cells transduced with CAR designated HER2-CD28TM-CD28-CD3.

Figure 10:
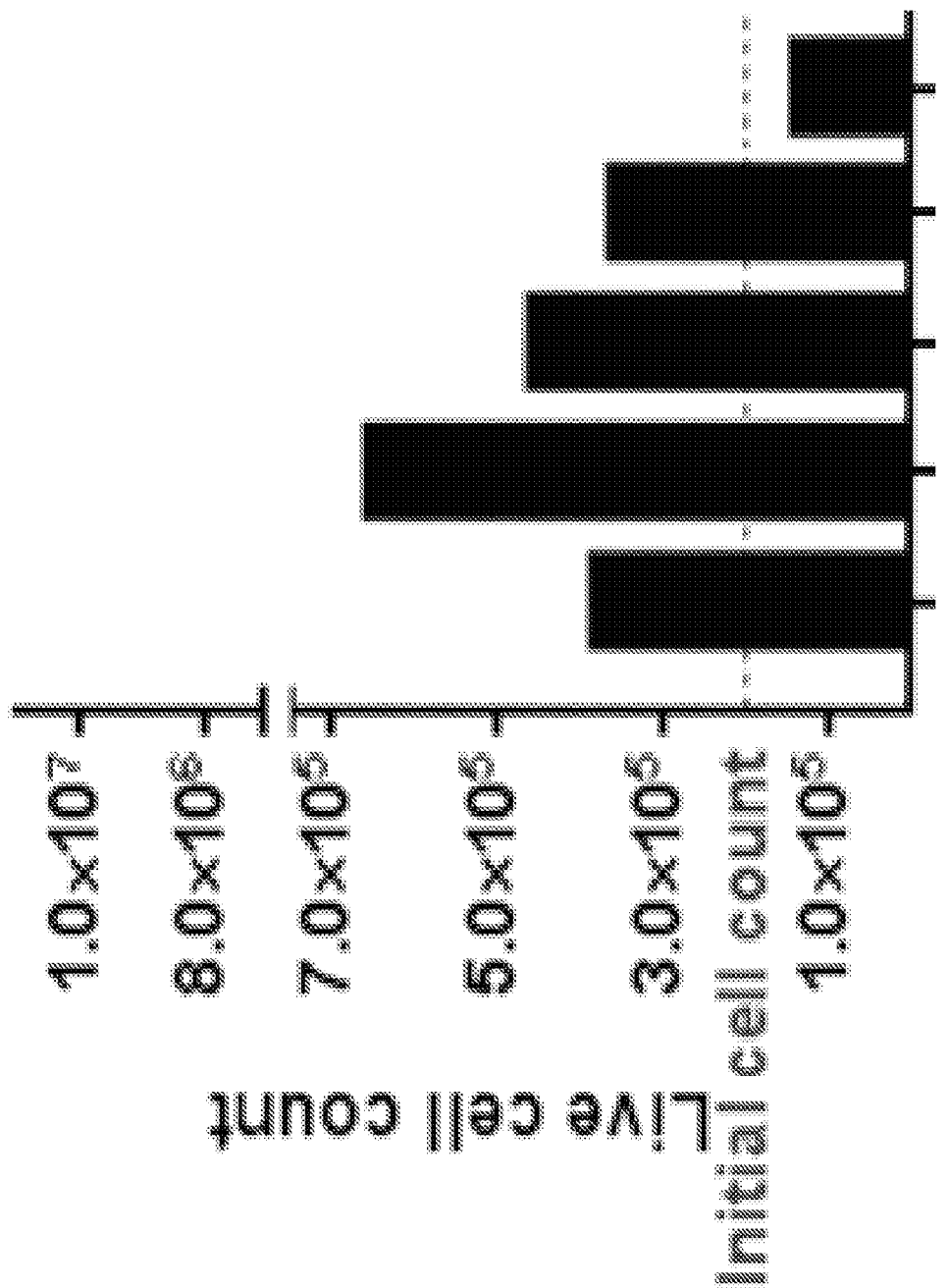

FIG. 10 depicts live T cell counts following stimulation with HER2-Fc. First (leftmost) bar: cells transduced with CAR designated HER2-CD28TM-CD28-CD3; second bar: cells transduced with CAR designated HER-PD1TM-CD28-CD3; third bar: cells transduced with CAR designated HER-CTLA4(189)TM-41BB-CD3; fourth bar: cells transduced with CAR designated HER-PD1TM-41BB-CD3; fifth (rightmost) bar: mock-transduced cells (no CAR expressed).

5. DETAILED DESCRIPTION

In one aspect, provided herein are polypeptides, e.g., chimeric antigen receptors (see, e.g., Eshhar, U.S. Pat. No. 7,741,465), that can be expressed by immune system cells, e.g., T lymphocytes (T cells), are membrane-bound in such immune system cells, and which comprise a transmembrane domain from an immune system protein that normally transmits an inhibitory signal to such immune system cells, e.g., a transmembrane domain from CTLA4 (Cytotoxic T-Lymphocyte Antigen 4 or Cytotoxic T-Lymphocyte Associated protein 4) or PD-1 (Programmed Cell Death-1). Further provided herein are nucleic acid sequences encoding the polypeptides described herein. Also provided herein are immune system cells, e.g., T lymphocytes (e.g., T cells), expressing such polypeptides.

The polypeptides provided herein comprise an extracellular domain that binds to an antigen, e.g., an antigen on a cell, a transmembrane domain, and an intracellular (cytoplasmic) signaling domain that transmits a primary activation signal to an immune cell. When the polypeptides provided herein are expressed on the surface of, e.g., a T lymphocyte, and when the extracellular domain of the CAR binds to an antigen, the intracellular signaling domain transmits a signal to the T lymphocyte to activate and/or proliferate, and, if the antigen is present on a cell surface, to kill the cell expressing the antigen. Because T lymphocytes require two signals in order to fully activate, a primary activation signal and a costimulatory signal, in certain embodiments, the polypeptides described herein can comprise a costimulatory domain such that binding of the antigen to the extracellular domain results in transmission of both a primary activation signal and a costimulatory signal.

The polypeptides, e.g., CARs, provided herein are functional, immune stimulatory polypeptides that comprise a transmembrane domain from a T cell co-inhibitory protein, e.g., CTLA4 or PD-1. In one aspect, provided herein is a polypeptide comprising (i) a transmembrane domain from CTLA4 or PD-1, (ii) an intracellular domain (e.g., cytoplasmic domain) of an endogenous protein expressed on the surface of lymphocytes and that triggers the activation and/or proliferation of said lymphocytes, and (iii) an extracellular domain that binds to an antigen, wherein if the transmembrane domain is from CTLA4, the intracellular domain and extracellular domain of said polypeptide are not from CTLA4; and if the transmembrane domain is from PD-1, the intracellular domain and extracellular domain of said polypeptide are not from PD-1. In a specific embodiment, a T lymphocyte expressing a polypeptide described herein is activated or stimulated to proliferate when said polypeptide binds to an antigen to which the polypeptide is specific (i.e., an antigen that is bound by the extracellular domain of the polypeptide). In a specific embodiment, the polypeptide, when expressed on the surface of a T lymphocyte, directs the T lymphocyte to kill a cell expressing said antigen.

In certain embodiments the polypeptides provided herein comprise a transmembrane domain from CTLA4 or PD-1, or a portion thereof, wherein the CTLA4 or PD-1 transmembrane domain is from a mammalian CTLA4 or PD-1, e.g., human, primate, or rodent, e.g., murine CTLA4 or PD-1. In a specific embodiment, the transmembrane domain does not comprise amino acids from the intracellular domain, extracellular domain, or either the intracellular or extracellular domain of CTLA4 or PD-1. Specific, non-limiting examples of CTLA4 or PD-1 transmembrane domain sequences are provided below.

In a specific embodiment, provided herein is a polypeptide comprising a transmembrane domain from CTLA4, wherein the CTLA4 transmembrane domain is the polypeptide sequence encoded by exon 3 of a human ctla4 gene (e.g., GenBank Accession No. NM_005214.4 (CTLA4 cytotoxic T-lymphocyte-associated protein 4 (*Homo sapiens*); Gene ID: 1493)).

In another specific embodiment, the CTLA4 transmembrane domain of a polypeptide provided herein is or comprises the amino acid sequence (SEQ ID NO: 1)
PEPCPDSDFLLWILAAVSSGLFFYSFLLTAVSLSKM (in three-letter code, Pro-Glu-Pro-Cys-Pro-Asp-Ser-Asp-Phe- Leu-Leu-Trp-Ile-Leu-Ala-Ala-Val-Ser-Ser-Gly-Leu- Phe-Phe-Tyr-Ser-Phe-Leu-Leu-Thr-Ala-Val-Ser-Leu- Ser-Lys-Met).

In another specific embodiment, the CTLA4 transmembrane domain of a polypeptide provided herein is or comprises the polypeptide sequence encoded by nucleotides 610-722 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence (SEQ ID NO: 2)
PDSDFLLWILAAVSSGLFFYSFLLTAVSL (in three-letter code, Pro-Asp-Ser-Asp-Phe-Leu-Leu-Trp-Ile-Leu-Ala- Ala-Val-Ser-Ser-Gly-Leu-Phe-Phe-Tyr-Ser-Phe-Leu- Leu-Thr-Ala-Val-Ser-Leu).

In another specific embodiment, the CTLA4 transmembrane domain of a polypeptide provided herein is or comprises the polypeptide sequence encoded by nucleotides 636-699 of GenBank Accession No. NM_005214.4 (CTLA4 cytotoxic T-lymphocyte-associated protein 4 (*Homo sapiens*); Gene ID: 1493).

In another specific embodiment, the CTLA4 transmembrane domain of a polypeptide provided herein is or comprises the amino acid sequence FLLWILAAVSSGLFFYSFLLTAV (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val) (SEQ ID NO:3).

In another specific embodiment, the CTLA4 transmembrane domain of a polypeptide provided herein is or comprises the polypeptide sequence FLLWILAAVSSGLFFYSFLLT (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr) (SEQ ID NO:4).

In another specific embodiment, the CTLA4 transmembrane domain of a polypeptide provided herein is or comprises the polypeptide sequence (SEQ ID NO: 5)
FLLWILVAVSLGLFFYSFLVSAVSLS (in three-letter code, Phe-Leu-Leu-Trp-Ile-Leu-Val-Ala-Val-Ser-Leu-Gly- Leu-Phe-Phe-Tyr-Ser-Phe-Leu-Val-Ser-Ala-Val-Ser- Leu-Ser).

In another specific embodiment, the CTLA4 transmembrane domain of a polypeptide provided herein is or comprises the polypeptide sequence (SEQ ID NO: 9)
LGIGNGTQIYVIDPEPSPDSDFLLWILAAVSSGLFFYSFLLTAVSLSKM (in three-letter code, Leu Gly Ile Gly Asn Gly Thr Gln Ile Tyr Val Ile Asp Pro Glu Pro Ser Pro Asp Ser Asp Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, the CTLA4 transmembrane domain of a polypeptide provided herein is or comprises the polypeptide sequence (SEQ ID NO: 10)
FLLWILAAVSSGLFFYSFLLTAVSLSKM (in three-letter code, Phe Leu Leu Trp Ile Leu Ala Ala Val Ser Ser Gly Leu Phe Phe Tyr Ser Phe Leu Leu Thr Ala Val Ser Leu Ser Lys Met).

In another specific embodiment, the PD-1 transmembrane domain of a polypeptide provided herein is or comprises the amino acid sequence (SEQ ID NO: 6)
TLVVGVVGGLLGSLVLLVWVLAVICSRAA (in three-letter code, Thr-Leu-Val-Val-Gly-Val-Val-Gly-Gly-Leu-Leu- Gly-Ser-Leu-Val-Leu-Leu-Val-Trp-Val-Leu-Ala-Val- Ile-Cys-Ser-Arg-Ala-Ala).

In another specific embodiment, the PD-1 transmembrane domain of a polypeptide provided herein is or comprises the amino acid sequence VGVVGGLLGSLVLLVWVLAVI (in three-letter code, Val-Gly-Val-Val-Gly-Gly-Leu-Leu-Gly-Ser-Leu-Val-Leu-Leu-Val-Trp-Val-Leu-Ala-Val-Ile) (SEQ ID NO:7).

In another specific embodiment, the PD-1 transmembrane domain of a polypeptide provided herein is or comprises the amino acid sequence (SEQ ID NO: 8)
FQTLVVGVVGGLLGSLVLLVWVLAVI (in three-letter code, Phe-Glu-Thr-Leu-Val-Val-Gly-Val-Val-Gly-Gly-Leu- Leu-Gly-Ser-Leu-Val-Leu-Leu-Val-Trp-Val-Leu-Ala- Val-Ile).

In another specific embodiment, the PD-1 transmembrane domain of a polypeptide provided herein is or comprises the amino acid sequence (SEQ ID NO: 11)
FQTLVVGVVGGLLGSLVLLVWVLAVICSRAA (in three-letter code, Phe Gln Thr Leu Val Val Gly Val Val Gly Gly Leu Leu Gly Ser Leu Val Leu Leu Val Trp Val Leu Ala Val Ile Cys Ser Arg Ala Ala).

As exemplified by the CTLA-4 and PD-1 transmembrane domain sequences described herein (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11), the transmembrane domains described herein, in certain embodiments, comprise one or more amino acids from the extracellular domain and/or one or more amino acids from the intracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1). In certain embodiments, the transmembrane domains described herein comprise 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1). In certain embodiments, the transmembrane domains described herein comprise (i) 1, 2, 3, 4, 5, 6, 7, 8, 9, 10, 11, 12, 13, 14, 15, 16, 17, 18, 19, 20, 21, 22, 23, 24, or 25 amino acids from the extracellular domain of the protein from which they are derived (i.e., CTLA-4 or PD-1) and (ii) 1, 2, 3, 4, 5, 6, 7, 8, 9, 10, 11, 12, 13, 14, 15, 16, 17, 18, 19, 20, 21, 22, 23, 24, or 25 amino acids from the intracellular domain of the protein from which they are derived (i.e., CTLA-4 or PD-1).

In another specific embodiment, provided herein is a polypeptide that comprises a transmembrane domain, wherein the transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a polypeptide that comprises a transmembrane domain, wherein the transmembrane domain is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In certain embodiments, provided herein is a nucleotide sequence that encodes one of the polypeptides disclosed herein. In a specific embodiment, provided herein is a nucleotide sequence that comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid that encodes a polypeptide described herein, wherein the nucleic acid comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another specific embodiment, provided herein is a nucleic acid sequence that encodes a polypeptide that is at least 75%, at least 80%, at least 85%, at least 90%, or at least 95%, identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In constructing the polypeptides provided herein, in certain embodiments, human sequences may be combined with non-human sequences. For example, a polypeptide comprising human extracellular and intracellular domain amino acid sequences may comprise a transmembrane domain from a non-human species; e.g., may comprise a murine CTLA4 transmembrane domain or a murine PD-1 transmembrane domain. In a more specific embodiment, the polypeptide comprises human amino acid sequences for the extracellular and intracellular domains, and comprises a transmembrane domain having, or consisting of, the amino acid sequence of SEQ ID NO:5.

The extracellular domains of the polypeptides provided herein bind to an antigen of interest. In certain embodiments, the extracellular domain of a polypeptide provided herein comprises a receptor, or a portion of a receptor, that binds to said antigen. The extracellular domain may be, e.g., a receptor, or a portion of a receptor, that binds to said antigen. In certain embodiments, the extracellular domain comprises, or is, an antibody or an antigen-binding portion thereof. In specific embodiments, the extracellular domain comprises, or is, a single-chain Fv domain. The single-chain Fv domain can comprise, for example, a $V_L$ linked to $V_H$ by a flexible linker, wherein said $V_L$ and $V_H$ are from an antibody that binds said antigen.

The antigen to which the extracellular domain of the polypeptides provided herein binds/recognizes can be any antigen of interest, e.g., can be an antigen on a tumor cell. The tumor cell may be, e.g., a cell in a solid tumor, or cell of a non-solid tumor, e.g., a cell of a blood cancer. The antigen can be any antigen that is expressed on a cell of any tumor or cancer type, e.g., cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma. Antigens specific to certain cancers, as well as methods for identifying such antigens, are known in the art.

In a specific embodiment, in which the cancer is chronic lymphocytic leukemia (CLL), the B cells of the CLL have a normal karyotype. In other specific embodiments, in which the cancer is chronic lymphocytic leukemia (CLL), the B cells of the CLL carry a 17p deletion, an 11q deletion, a 12q trisomy, a 13q deletion or a p53 deletion.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAP1 (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein.

In certain embodiments, the TAA or TSA recognized by the extracellular domain of a polypeptide described herein is integrin αvβ3 (CD61), galactin, or Ral-B.

In certain embodiments, the TAA or TSA recognized by the extracellular domain of a polypeptide described herein is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXB1, SPA17, SSX, SYCP1, or TPTE.

In certain other embodiments, the TAA or TSA recognized by the extracellular domain of a polypeptide described herein is a carbohydrate or ganglioside, e.g., fuc-GM1, GM2 (oncofetal antigen-immunogenic-1; OFA-I-1); GD2 (OFA-I-2), GM3, GD3, and the like.

In certain other embodiments, the TAA or TSA recognized by the extracellular domain of a polypeptide described herein is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel 17), tyrosinase, TRP-1, TRP-2, MAGE-1, MAGE-3, RAGE, GAGE-1, GAGE-2, p15(58), RAGE, SCP-1, Hom/Mel-40, PRAME, p53, H-Ras, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1 antigen, NuMa, K-ras, Mum-1, p16, TAGE, PSMA, CT7, telomerase, 43-9F, 5T4, 791Tgp72, β-HCG, BCA225, BTAA, CD68\KP1, CO-029, FGF-5, G250, Ga733 (Ep-CAM), HTgp-175, M344, MA-50, MG7-Ag, Ca-MOv18, NB\70K, NY-CO-1, RCAS1, SDCCAG16, TA-90, TAAL6, TAG72, TLP, or TPS. Other tumor-associated and tumor-specific antigens are known to those in the art.

Antibodies, and scFvs, that bind to TSAs and TAAs are known in the art, as are nucleotide sequences that encode them.

In certain specific embodiments, the antigen recognized by the extracellular domain of a polypeptide described herein is an antigen not considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

In certain embodiments, the extracellular domain of the polypeptides described herein is joined to the transmembrane domain of the polypeptide by a linker, spacer or hinge polypeptide sequence, e.g., a sequence from CD28 or a sequence from CTLA4.

In certain embodiments, the intracellular domain of a polypeptide described herein is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit.

In certain embodiments, the polypeptides provided herein additionally comprise one or more co-stimulatory domains or motifs, e.g., as part of the intracellular domain of the polypeptide. The one or more co-stimulatory domains or motifs can be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif.

In a specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 or CTLA4 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CH2CH3 hinge polypeptide sequence; (iii) a CTLA4 or PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a CD28 hinge polypeptide sequence; (iii) a CTLA4 or PD-1 transmembrane domain; (iv) a 4-1BB costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) an antigen-binding domain (e.g., an antigen binding domain that binds an antigen on a tumor cell, e.g., an antigen on a tumor cell described above); (ii) a PD-1 hinge polypeptide sequence; (iii) a CTLA4 or PD-1 transmembrane domain; (iv) a costimulatory domain; and (v) an intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a PD-1 transmembrane domain; (iv) a CD28 costimulatory domain; and (v) a CD3ζ intracellular signaling domain.

In another specific embodiment, a polypeptide provided herein comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a CTLA4 transmembrane domain; (iv) a 4-1BB costimulatory domain; and (v) a CD3ζ intracellular signaling domain.

In another specific embodiment, the polypeptide comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CD28 hinge polypeptide sequence; (iii) a PD-1 transmembrane domain; (iv) a 4-1BB costimulatory domain; and (v) a CD3ζ intracellular signaling domain.

In another specific embodiment, the polypeptide comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a CTLA4 hinge polypeptide sequence; (iii) a PD-1 transmembrane domain; (iv) a 4-1BB costimulatory domain; and (v) a CD3ζ intracellular signaling domain.

In another specific embodiment, the polypeptide comprises, in order, from N-terminus to C-terminus: (i) a single-chain Fv domain comprising a $V_L$ linked to $V_H$ by a linker, wherein said $V_L$ and $V_H$ are from an antibody that binds an antigen of interest (e.g., an antigen on a tumor cell, e.g., an antigen on a tumor cell described above); (ii) a PD-1 hinge polypeptide sequence; (iii) a CTLA4 transmembrane domain; (iv) a 4-1BB costimulatory domain; and (v) a CD3ζ intracellular signaling domain.

5.1. Isolated Polypeptides (Chimeric Antigen Receptors)

The T lymphocyte-stimulatory polypeptides provided herein, which comprise a CTLA4 or PD-1 transmembrane domain, may be modified by, e.g., acylation, amidation, glycosylation, methylation, phosphorylation, sulfation, sumoylation, ubiquitylation, or the like. The polypeptides may be labeled with a label capable of providing a detectable signal, e.g., with radioisotopes and fluorescent compounds. One or more side chains of the first or second polypeptides may be derivatized, e.g., derivatization of lysinyl and amino terminal residues with succinic or other carboxylic acid anhydrides, or derivatization with, e.g., imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N═C═N—R') such as 1-cyclohexyl-3-(2-morpholinyl-(4-ethyl)carbodiimide or 1-ethyl-3-(4-azonia-4,4-dimethylpentyl)carbodiimide.

5.2. Isolated Nucleic Acids

Provided herein are nucleic acid sequences (polynucleotides) that encode one or more of the polypeptides provided herein. The polynucleotides may be contained within any polynucleotide vector suitable for the transformation of immune cells, e.g., T lymphocytes. For example, T lymphocytes may be transformed using synthetic vectors, lentiviral or retroviral vectors, autonomously replicating plasmids, a virus (e.g., a retrovirus, lentivirus, adenovirus, or herpes virus), or the like, containing polynucleotides encoding the first and second polypeptides (e.g., chimeric receptors).

Lentiviral vectors suitable for transformation of T lymphocytes include, but are not limited to, e.g., the lentiviral vectors described in U.S. Pat. Nos. 5,994,136; 6,165,782; 6,428,953; 7,083,981; and 7,250,299, the disclosures of which are hereby incorporated by reference in their entireties. HIV vectors suitable for transformation of T lymphocytes include, but are not limited to, e.g., the vectors described in U.S. Pat. No. 5,665,577, the disclosure of which is hereby incorporated by reference in its entirety.

Nucleic acids useful in the production of the first and second polypeptides, e.g., within a modified T lymphocyte, include DNA, RNA, or nucleic acid analogs. Nucleic acid analogs can be modified at the base moiety, sugar moiety, or phosphate backbone, and can include deoxyuridine substitution for deoxythymidine, 5-methyl-2'-deoxycytidine or 5-bromo-2'-deoxycytidine substitution for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chain. 4:5-23. In addition, the deoxyphosphate backbone can be replaced with, for example, a phosphorothioate or phosphorodithioate backbone, a phosphoroamidite, or an alkyl phosphotriester backbone.

5.3. T Lymphocytes

Provided herein are immune cells, e.g., T lymphocytes, comprising the polypeptides provided herein. The T lymphocytes provided herein may be naive T lymphocytes or MHC-restricted T lymphocytes. In certain embodiments, the T lymphocytes provided herein are tumor infiltrating lymphocytes (TILs). In certain embodiments, the T lymphocytes provided herein have been isolated from a tumor biopsy, or have been expanded from T lymphocytes isolated from a tumor biopsy. In certain other embodiments, the T lymphocytes provided herein have been isolated from, or expanded from, T lymphocytes expanded from, peripheral blood, cord blood, or lymph.

In certain embodiments, the immune cells provided herein that comprise a polypeptide provided herein, e.g., modified T lymphocytes, are autologous to an individual to whom the modified T lymphocytes are to be administered. In certain embodiments, the modified T lymphocytes provided herein are allogeneic to an individual to whom the modified T lymphocytes are to be administered. Where allogeneic T lymphocytes are used to prepare modified T lymphocytes, T lymphocytes can be selected that will reduce the possibility of graft-versus-host disease (GVHD) in the individual. For example, in certain embodiments, virus-specific T lymphocytes can be selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

In one embodiment, T lymphocytes are obtained from an individual, optionally expanded, and then transformed with a polynucleotide encoding a CTLA4 or PD-1 transmembrane domain-containing polypeptide described herein, and optionally expanded. In another embodiment, T lymphocytes are obtained from an individual, optionally then expanded, and then transformed with a polynucleotide encoding a CTLA4 or PD-1 transmembrane domain-containing polypeptide described herein, and optionally then expanded at least one more time. Cells containing the polynucleotides may be selected using a selectable marker.

In certain embodiments, the modified T lymphocytes described herein express or comprise native TCR proteins, e.g., TCR-α and TCR-β that are capable of forming native TCR complexes, in addition to the CTLA4 or PD-1 transmembrane domain-containing polypeptide. In certain other embodiments, either or both of the native genes encoding TCR-α and TCR-β in the modified T lymphocytes are modified to be non-functional, e.g., a portion or all are deleted, a mutation is inserted, etc.

In certain embodiments, the T lymphocytes described herein are isolated from a tumor lesion, e.g., are tumor-infiltrating lymphocytes; such T lymphocytes are expected to be specific for a TSA or TAA.

In certain embodiments, the signaling motifs of the CTLA4 or PD-1 transmembrane domain-containing polypeptide, e.g., CAR, can be used to promote proliferation and expansion of the modified T lymphocytes described herein. For example, unmodified T lymphocytes, and T lymphocytes comprising a polypeptide comprising a CD3t signaling domain and a CD28 co-stimulatory domain can be expanded using antibodies to CD3 and CD28, e.g., antibodies attached to beads, or to the surface of a cell culture plate; see, e.g., U.S. Pat. Nos. 5,948,893; 6,534,055; 6,352,694; 6,692,964; 6,887,466; and 6,905,681. In certain embodiments, the antigen, to which the extracellular domain of the CTLA4 or PD-1 transmembrane domain-containing polypeptide binds, can be used to promote selective expansion of T lymphocytes expressing the polypeptide. For example, in one embodiment, in which the antigen is a TSA, T lymphocytes comprising the polypeptide cultured in the presence of the TSA, e.g., a soluble form of the TSA, resulting in increased proliferation as compared to culturing in the absence of the TSA.

In certain embodiments, T lymphocytes comprising a CTLA4 or PD-1 transmembrane domain-containing polypeptide described herein are stimulated to proliferate using an antibody that binds to a signaling domain on the polypeptide coupled with the antigen that can be bound by the extracellular antigen-binding domain of the polypeptide. For example, in embodiments in which the polypeptide's signaling domain is CD3ζ and the antigen that binds to the polypeptide is a TSA, T lymphocytes comprising the polypeptide are stimulated to proliferate by culturing the cells in the presence of the TSA (e.g., a soluble form of the TSA) in combination with an antibody that binds to CD3ζ.

In any of the above embodiments, the antigen and/or antibody can exist free in the medium in which the T lymphocytes are cultures, or either or both can be attached to a solid support, e.g., tissue culture plastic surface, beads, or the like.

The T lymphocytes comprising a CTLA4 or PD-1 transmembrane domain-containing polypeptide described herein can optionally comprise a "suicide gene" or "safety switch" that enables killing of all or substantially all of the T lymphocytes when desired. For example, the modified T lymphocytes described herein, in certain embodiments, can comprise an HSV thymidine kinase gene (HSV-TK), which causes death of the modified T lymphocytes upon contact with gancyclovir. In another embodiment, the modified T lymphocytes express or comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 105(11):4247-4254 (2005).

5.4. Methods of Using Modified T Lymphocytes

The modified immune cells, e.g., the modified T lymphocytes, provided herein that comprise a CTLA4 or PD-1 transmembrane domain-containing polypeptide, e.g., CAR, can be used to treat an individual having one or more types of cells desired to be targeted by T lymphocytes, e.g., one or more types of cells to be killed. In certain embodiments, the cells to be killed are cancer cells, e.g., tumor cells. In certain embodiments, the cancer cells are cells of a solid tumor. In certain embodiments, the cells are cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

Efficacy of the modified T lymphocytes described herein, after administration to an individual having a disease or disorder remediable by T lymphocytes, e.g., an individual having cancer, can be assessed by one or more criteria, specific to the particular disease or disorder, known to those of ordinary skill in the art, to be indicative of progress of the disease or disorder. Generally, administration of the modified T lymphocytes described herein to such an individual is effective when one or more of said criteria detectably, e.g., significantly, moves from a disease state value or range to, or towards, a normal value or range.

The modified T lymphocytes described herein may be formulated in any pharmaceutically-acceptable solution, preferably a solution suitable for the delivery of living cells, e.g., saline solution (such as Ringer's solution), gelatins, carbohydrates (e.g., lactose, amylose, starch, or the like), fatty acid esters, hydroxymethylcellulose, polyvinyl pyrolidine, etc. Such preparations are preferably sterilized prior to addition of the modified T lymphocytes, and may be mixed with auxiliary agents such as lubricants, preservatives, stabilizers, emulsifiers, salts for influencing osmotic pressure, buffers, and coloring. Pharmaceutical carriers suitable for use in formulating the modified T lymphocytes are known in the art and are described, for example, in WO 96/05309.

In certain embodiments, the modified T lymphocytes described herein are formulated into individual doses, wherein said individual doses comprise at least, at most, or about $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, or $1 \times 10^{11}$ modified T lymphocytes. In certain embodiments, the modified T lymphocytes are formulated for intravenous, intraarterial, parenteral, intramuscular, subcutaneous, intrathecal, or intraocular administration, or administration within a particular organ or tissue.

6. EXAMPLES

6.1. Example 1: Treatment of B Cell Lymphoma

An individual presents with B-cell chronic lymphocytic leukemia, a B cell lymphoma. Testing of B cells from the individual determines that the B cells carry a 17p deletion. T lymphocytes are obtained from the individual, transfected with a lentiviral vector comprising a nucleotide sequence that encodes a chimeric antigen receptor (CAR), and expanded using CD3+CD28-coated beads to sufficient numbers for administration. The chimeric receptor comprises an extracellular antigen-binding region that binds to CD19; a transmembrane domain from CTLA4; an intracellular costimulatory domain from CD28; and an intracellular CD3ζ domain. The individual is administered between $10^9$ and $10^{10}$ of the T lymphocytes in a 200 ml saline solution by intravenous infusion over 30 minutes. The individual is monitored for two weeks afterwards to establish a reduction of at least 90% of CD19+ B cells in the individual's blood.

6.2. Example 2: Treatment of a B Cell Lymphoma

An individual presents with B-cell chronic lymphocytic leukemia, a B cell lymphoma. Testing of B cells from the individual determines that the B cells carry a 17p deletion. About $10^6$ T lymphocytes are obtained from the individual, transfected with a lentiviral vector comprising a nucleotide sequence that encodes a CAR. The CAR comprises an extracellular antigen-binding region that binds to CD19; a transmembrane domain from PD-1; an intracellular costimulatory domain from CD28; and an intracellular CD3ζ domain. CAR-expressing T cells are administered to the individual without prior expansion of the T cells. The individual is administered between $10^5$ and $10^6$ of the T lymphocytes in 200 ml saline solution by intravenous infusion over 30 minutes. The individual is monitored for two weeks afterwards to establish a reduction of at least 90% of CD19+ B cells in the individual's blood.

6.3. Example 3: Treatment of B Cell Lymphoma

An individual presents with B-cell chronic lymphocytic leukemia, a B cell lymphoma. Testing of B cells from the individual determines that the B cells carry a p53 deletion. T lymphocytes are obtained from the individual, transfected with a lentiviral vector comprising a nucleotide sequence that encodes a CAR, and expanded using CD3+CD28-coated beads to sufficient numbers for administration. The CAR comprises an extracellular antigen-binding region that binds to CD19; a transmembrane domain from CTLA4; intracellular co-stimulatory domains from each of CD28, 4-1BB, and OX40; and an intracellular CD3ζ domain. The individual is administered between $10^9$ and $10^{10}$ of the T lymphocytes in 200 ml saline solution by intravenous infusion over 30 minutes. The individual is monitored for two weeks afterwards to establish a reduction of at least 90% of CD19+ B cells in the individual's blood.

6.4. Example 4: Treatment of a B Cell Lymphoma

An individual presents with B-cell chronic lymphocytic leukemia, a B cell lymphoma. Testing of B cells from the individual determines that the B cells carry a p53 deletion. About $10^6$ T lymphocytes are obtained from the individual, transfected with a lentiviral vector comprising a nucleotide sequence that encodes a CAR. The CAR comprises an extracellular antigen-binding region that binds to CD19; a transmembrane domain from PD-1; intracellular co-stimulatory domains from each of CD28, 4-1BB, and OX40; and an intracellular CD3t domain. CAR-expressing T cells are administered to the individual without prior expansion of the T cells. The individual is administered between $10^5$ and $10^6$ of the T lymphocytes in 200 ml saline solution by intravenous infusion over 30 minutes. The individual is monitored for two weeks afterwards to establish a reduction of at least 90% of CD19+ B cells in the individual's blood.

6.5. Example 5: Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from CTLA4, an intracellular co-stimulatory domain from CD28, and an intracellular CD3ζ domain. The individual is re-assessed for prostate cancer stage and spread to lymph nodes, and histology of biopsied prostate tissue is performed, at 30, 60 and 90 days post-administration.

6.6. Example 6: Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from PD-1, an intracellular co-stimulatory domain from CD28, and an intracellular CD3ζ domain. The individual is re-assessed for prostate cancer stage and spread to lymph nodes, and histology of biopsied prostate tissue is performed, at 30, 60 and 90 days post-administration.

6.7. Example 7: Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from CTLA-4, intracellular co-stimulatory domains from each of CD28, 4-1BB, and OX40, and an intracellular CD3ζ domain. The individual is re-assessed for prostate cancer stage and spread to lymph nodes, and histology of biopsied prostate tissue is performed, at 30, 60 and 90 days post-administration.

6.8. Example 8: Treatment of Prostate Cancer

An individual presents with stage T2 prostate cancer, with no spread to regional or other lymph nodes (N0, M0). Histological grade is determined to be G2. Overall, the individual is determined to have Stage I1 prostate cancer. The individual is administered between $10^9$ and $10^{10}$ modified T lymphocytes that comprise a CAR, in 200 ml saline solution by intravenous infusion over 30 minutes. The CAR comprises an extracellular antigen-binding region that binds to PSCA, a transmembrane domain from PD-1, intracellular co-stimulatory domains from each of CD28, 4-1BB, and OX40, and an intracellular CD3ζ domain. The individual is re-assessed for prostate cancer stage and spread to lymph nodes, and histology of biopsied prostate tissue is performed, at 30, 60 and 90 days post-administration.

6.9. Example 9: CARs Comprising a CTLA-4 or PD-1 Transmembrane Domain

This example demonstrates that a chimeric antigen receptor comprising a CTLA-4 or PD-1 transmembrane domain is functional and active in T cells.

6.9.1 CARs Comprising a CTLA-4 Transmembrane Domain

CARs comprising an extracellular domain (anti-HER2 scFV) that binds the antigen HER2 were generated. Specifically, the following CARs were generated: (i) HER-28TMζ, comprising an Anti-HER2 scFV, a CD28 transmembrane domain, and a CD3ζ intracellular domain; (ii) HER-28TM28ζ, comprising an Anti-HER2 scFV, a CD28 transmembrane domain, and a CD28-CD3ζ intracellular domain; (iii) HER2-CTLA4TM28ζ, comprising an Anti-HER2 scFV, a CH2CH3 hinge, a CTLA-4 transmembrane domain (SEQ ID NO:10), and a CD28-CD3ζ intracellular domain; and (iv) HER2-41BBTM28ζ, comprising an Anti-HER2 scFV, a CD8 hinge, a 4-1BB transmembrane domain, and a CD28-CD3ζ intracellular domain.

The ability of human T cells to express the CARs described above was assessed. Pan T cells and naïve Pan T cells were isolated from buffy coat of donor sample blood by negative selection using a human Pan T isolation Kit II and human naïve Pan T isolation kit, respectively (Miltenyi, Cambridge, Mass.). Isolated T cells were cultured in RPMI complete media in the presence of 10 ng/ml IL-7 for 11 days, and then transduced with lentivirus expressing CAR constructs at MOI of 5.

Three days after transduction, CAR T cell phenotype was characterized staining the cells with a HER2-Fc fusion protein (R&D Systems, Minneapolis, Minn.), followed by staining with a polyclonal goat anti-human IgG-Fc antibody conjugated with FITC or APC) (Jackson ImmunoRessearch, West Grove, Pa.). On the same day, T cells were stimulated with HER2-Fc fusion protein at a gradient of concentrations ranging from 0.25 µg/ml to 1 µg/ml. Supernatant was collected 48 hours post-stimulation for cytometric beads array (CBA) analysis, to assess cytokine production by the T cells, using a customized CBA flex set (BD Biosciences, San Jose, Calif.). The cells from the culture after supernatant removal were stained for measurement of T cell activation surface markers CD69, 4-1BB, CD71, HLA-DR, and CD25 using anti-human monoclonal antibodies with fluorochrome conjugates (BD Biosciences). Flow cytometric analysis for both CBA and surface markers was performed on a FACS Canto II machine and data were acquired with FACSDiva software (BD Biosciences). The CBA data were analyzed with FCAP Assay software (Soft Flow Ltd., Pecs, Hungary). Surface marker flow data were analyzed using FlowJo flow cytometry software (Tree Star, Ashland, Oreg.).

Figure 1:
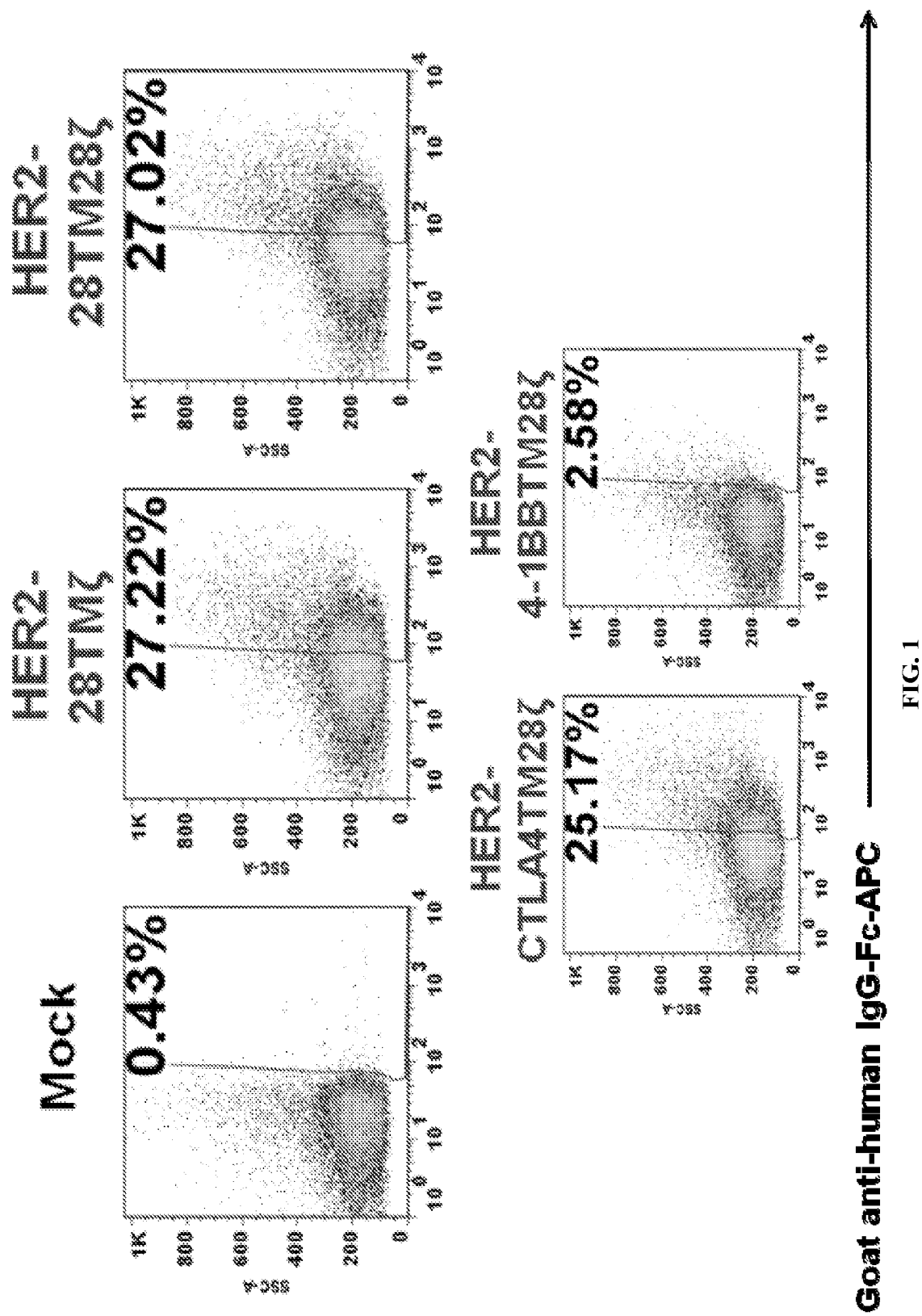
FIG. 1 depicts expression of CARs by T cells three days after transduction of the T cells with lentiviral vectors that express the CARS.

As shown in FIG. 1, three of the CARs generated, including the CAR having a CTLA-4 transmembrane domain, were highly expressed by the T cells. T cell activation surface markers CD69, 4-1BB, and HLA-DR each were upregulated upon CAR ligation, i.e., when the CAR T cells were stimulated with HER2-Fc fusion protein. In each case, the highest levels were observed in CAR T cells expressing the construct HER2-CTLA4TM28ζ.

Figure 2:
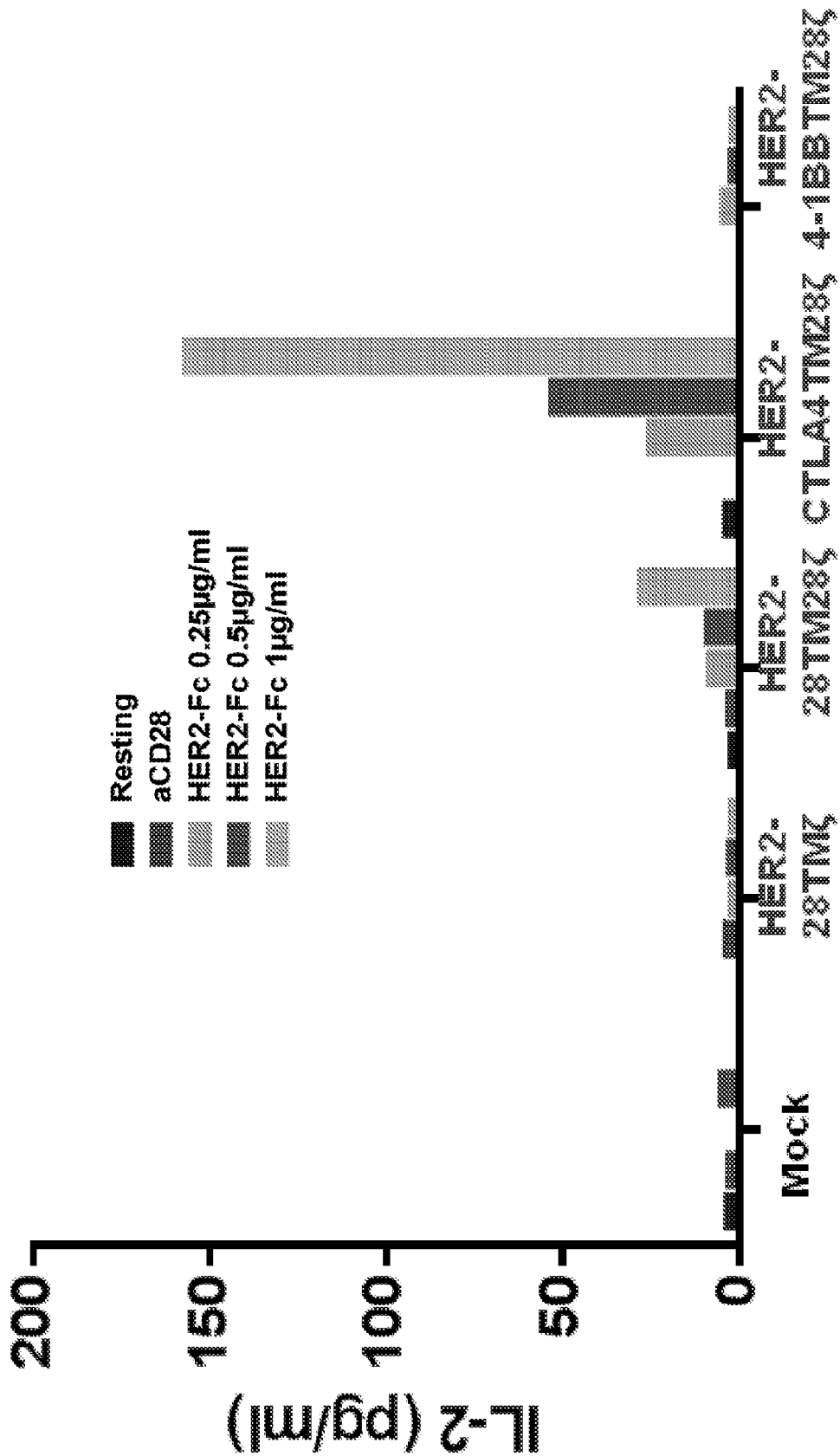
FIG. 2 depicts interleukin-2 (IL-2) production by CAR T cells (i) in the resting state (first bar), (ii) after exposure to anti-CD28 (second bar); (iii) after exposure to 0.25 μg/ml HER2-Fc; (iv) after exposure to 0.5 μg/ml HER2-Fc; and (v) after exposure to 1.0 μg/ml HER2-Fc.
Figure 3:
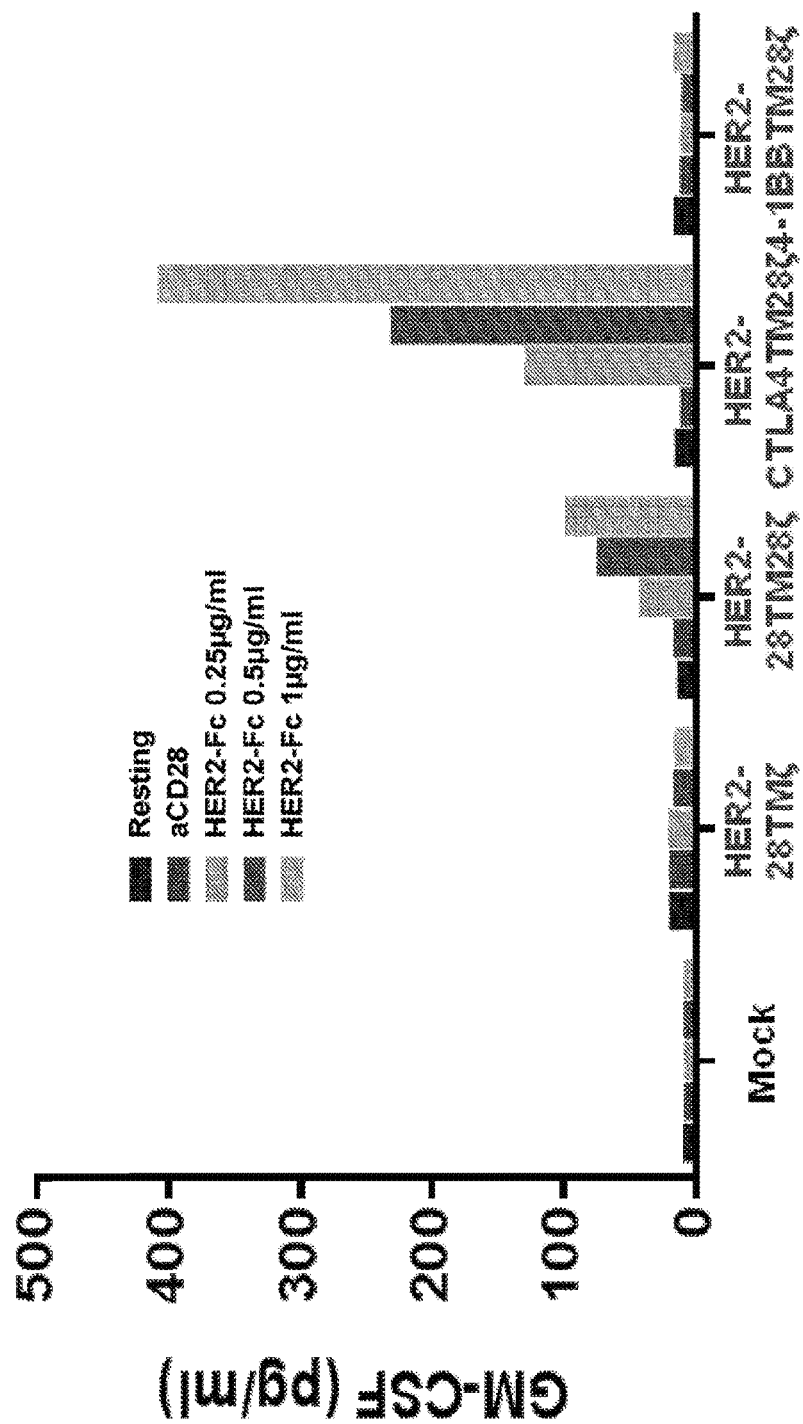
FIG. 3 depicts GM-CSF production by CAR T cells (i) in the resting state (first bar), (ii) after exposure to aCD28 (second bar); (iii) after exposure to 0.25 μg/ml HER2-Fc; (iv) after exposure to 0.5 μg/ml HER2-Fc; and (v) after exposure to 1.0 μg/ml HER2-Fc.
Figure 4:
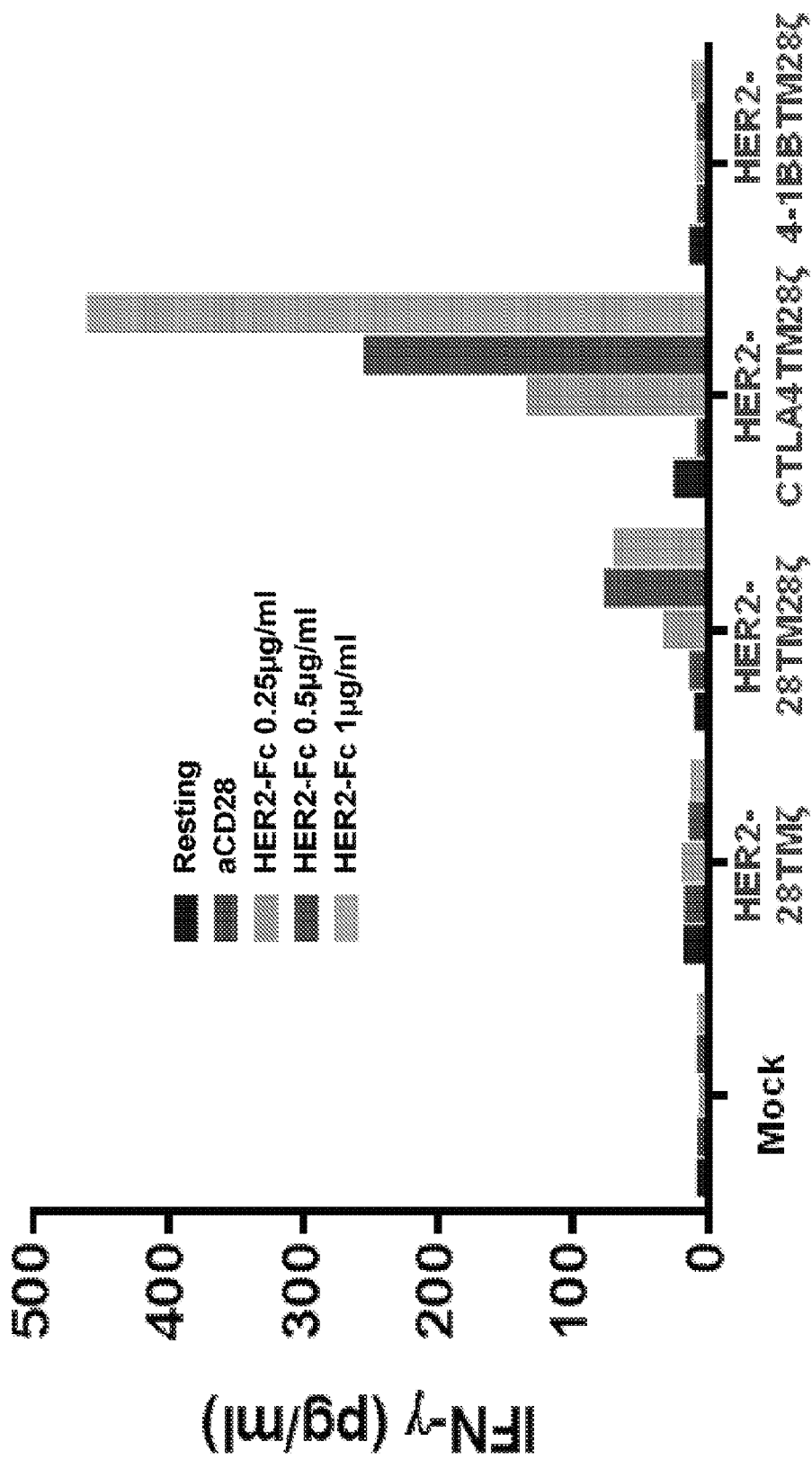
FIG. 4 depicts interferon-gamma (IFN-γ) production by CAR T cells (i) in the resting state (first bar), (ii) after exposure to aCD28 (second bar); (iii) after exposure to 0.25 μg/ml HER2-Fc; (iv) after exposure to 0.5 μg/ml HER2-Fc; and (v) after exposure to 1.0 μg/ml HER2-Fc.

As shown in FIGS. 2-4, two of the four sets of CART cells demonstrated cytokine production in response to HER2 stimulation. Specifically, T cells expressing the CAR designated HER2-28TM28ζ and T cells expressing the CAR designated HER2-CTLA4TM28ζ produced the cytokines interleukin-2 (IL-2) (FIG. 2), GM-CSF (FIG. 3), and interferon-gamma (IFN-γ) (FIG. 4) in a dose-dependent manner in response to HER2 stimulation. Surprisingly, T cells expressing a CAR comprising a transmembrane domain from a protein that normally transmits an inhibitory signal to immune system cells (i.e., CTLA-4 transmembrane domain) produced a much higher level of each cytokine as compared to T cells expressing each of the other CARs, including T cells expressing the CAR designated HER2-28TM28ζ. See FIGS. 2-4.

Figure 5:
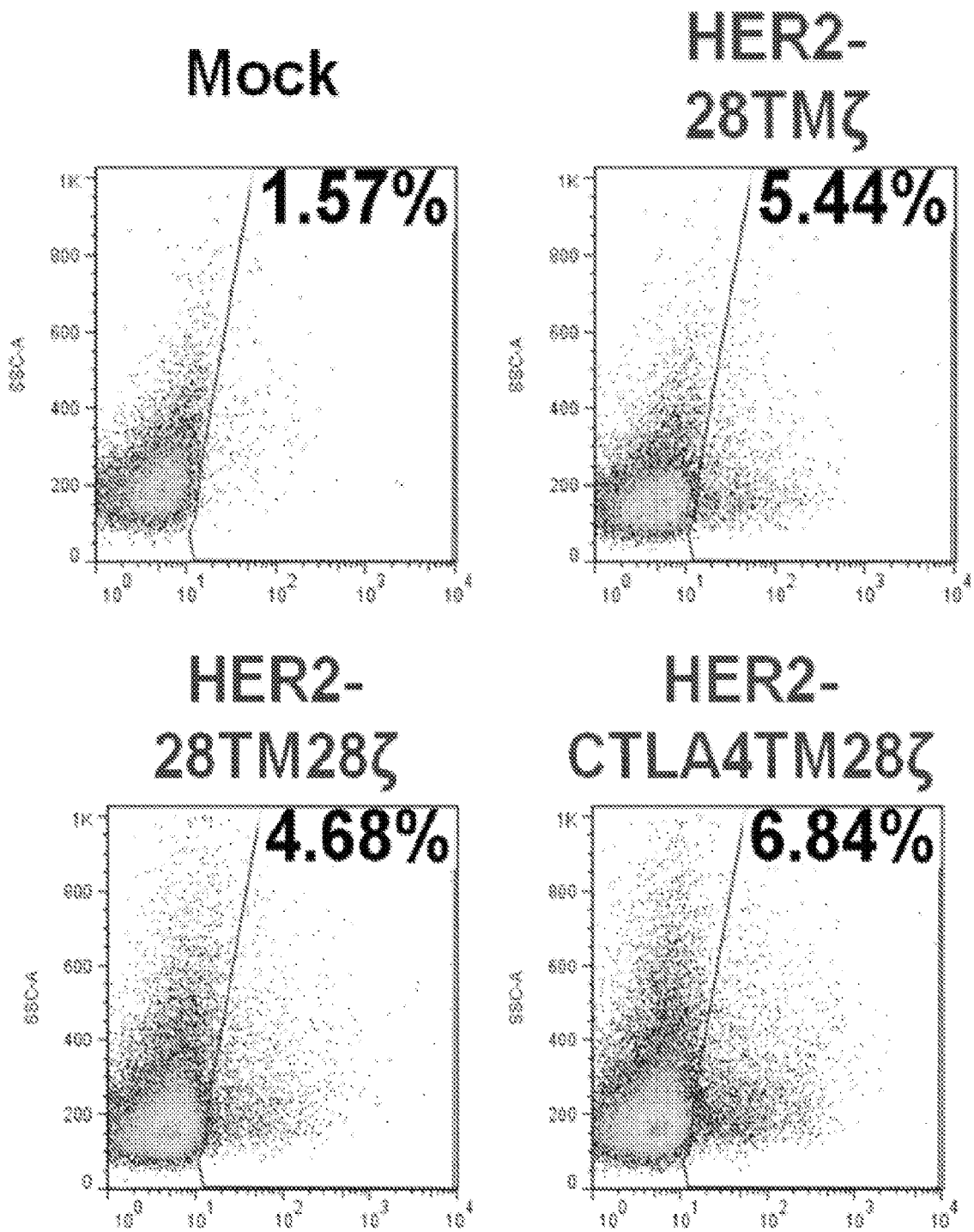
FIG. 5 depicts intracellular tumor necrosis factor alpha (TNF-α) production by CAR T cells after multiple rounds of exposure to 1.0 μg/ml HER2-Fc.

It further was examined whether stimulation of T cells expressing the CARs described above with HER2 induces intracellular tumor necrosis factor-alpha (TNF-α) production by the T cells. The CAR T cells were stimulated with HER2-Fc (1 µg/ml) for 2 days in medium containing IL-2 (50 IU/ml). The HER2 stimulation was performed two more times, separated by seven days each time. After the third stimulation, intracellular TNF-α was examined by flow cytometry. As shown in FIG. 5, T cells expressing the CAR designated HER2-28TM28ζ, T cells expressing the CAR designated HER2-CTLA4TM28κ, and T cells expressing the CAR designated HER2-28TMζ produced TNF-α, with the highest amount of TNF-α produced by T cells expressing a CAR comprising a transmembrane domain from a protein that normally transmits an inhibitory signal to immune system cells (i.e., CTLA-4 transmembrane domain).

Finally, it was determined whether stimulation of T cells expressing the CARs described above with HER2 results in enrichment of the CAR T cell populations. CAR T cells expressing the CARs described above were stimulated with HER2-Fc fusion protein. Thirteen days post-stimulation with HER2, CAR T cells were analyzed by flow cytometry, as described above. Surprisingly, as shown in FIGS. 6A-6B, only CAR T cells expressing the CAR designated HER2-CTLA4TM28ζ were enriched following HER2 stimulation.

6.9.2 CARs Comprising a PD-1 or CTLA-4 Transmembrane Domain

This example demonstrates that a chimeric antigen receptor comprising a CTLA-4 transmembrane domain or a PD-1 transmembrane domain is functional and active in T cells. CARs comprising an extracellular domain (anti-HER2 scFV) that binds the antigen HER2 were generated. Specifically, the following CARs were generated: (i) HER-PD1TM-CD28-CD3, comprising an Anti-HER2 scFV, a CH2CH3 hinge, a PD-1 transmembrane domain (SEQ ID NO:11), and a CD28-CD3 intracellular domain; (ii) HER-CTLA4(189)TM-41BB-CD3, comprising an Anti-HER2 scFV, a CD28 hinge, a CTLA-4 transmembrane domain (SEQ ID NO:10), and a 4-1BB-CD3 intracellular domain; (iii) HER-PD1TM-41BB-CD3, comprising an Anti-HER2 scFV, a CD28 hinge, a PD-1 transmembrane domain (SEQ ID NO:11), and a 4-1BB-CD3 intracellular domain; and (iv) HER2-CD28TM-CD28-CD3, comprising an Anti-HER2 scFV, a CD28 hinge, a CD28 transmembrane domain, and a CD28-CD3ζ intracellular domain.

Pan T cells and naïve Pan T cells were isolated from buffy coat of donor sample blood by negative selection using a human Pan T isolation Kit II and human naïve Pan T isolation kit, respectively (Miltenyi, Cambridge, Mass.). Isolated T cells were cultured in RPMI complete media in the presence of 10 ng/ml IL-7 for 11 days, and then transduced with lentivirus expressing CAR constructs at MOI of 7.

Three days after transduction, CAR T cell phenotype was characterized staining the cells with a HER2-Fc fusion protein (R&D Systems, Minneapolis, Minn.), followed by staining with a polyclonal goat anti-human IgG-Fc antibody conjugated with FITC or APC) (Jackson ImmunoRessearch, West Grove, Pa.). On the same day, T cells were stimulated with HER2-Fc fusion protein at a gradient of concentrations ranging from 0.25 µg/ml to 1 µg/ml. Supernatant was collected 48 hours post-stimulation for cytometric beads array (CBA) analysis, to assess cytokine production by the T cells, using a customized CBA flex set (BD Biosciences, San Jose, Calif.). The cells from the culture after supernatant removal were stained for measurement of T cell activation surface markers CD69, 4-1BB, CD71, HLA-DR, and CD25 using anti-human monoclonal antibodies with fluorochrome conjugates (BD Biosciences). Flow cytometric analysis for both CBA and surface markers was performed on a FACS Canto II machine and data were acquired with FACSDiva software (BD Biosciences). The CBA data were analyzed with FCAP Assay software (Soft Flow Ltd., Pecs, Hungary). Surface marker flow data were analyzed using FlowJo flow cytometry software (Tree Star, Ashland, Oreg.).

As shown in FIG. 7, each of the CARs generated were highly expressed by the T cells. T cell activation surface markers CD69, CD71, and HLA-DR each were upregulated upon stimulation of the above-described CAR T cells with HER2. In each case, the observed levels of upregulation were highest in CAR T cells expressing CARs with either a PD-1 or a CTLA-4 transmembrane domain.

As shown in FIGS. 8-9, the CAR T cells demonstrated cytokine production in response to HER2 stimulation. Specifically, T cells expressing the CARs described above produced the cytokines IL-2 (FIG. 8), TNF-α (FIG. 8), and IFN-γ (FIG. 8), GM-CSF (FIG. 9), Granzyme B (FIG. 9), and IL-13 (FIG. 9) in a dose-dependent manner in response to HER2 stimulation. In each case, T cells expressing CARs comprising a PD-1 or CTLA-4 transmembrane domain exhibited the highest levels of cytokine production, with T cells expressing the CAR designated HER-PD1TM-CD28-CD3 consistently producing the highest levels of each cytokine (see FIGS. 8 and 9).

Finally, it was determined whether stimulation of T cells expressing the CARs described above with HER2 results in enrichment of the CAR T cell populations. CAR T cells expressing the CARs described above were stimulated with HER2-Fc fusion protein. Eleven days post-stimulation with HER2, CAR T cells were analyzed by flow cytometry, as described above. As shown in FIG. 10, CAR T cells expressing the CAR designated HER-PD1TM-CD28-CD3 were enriched following HER2 stimulation, with T cells expressing the other CARs described showing modest levels of increase in live cells over the initial cell number.

6.9.3 Conclusion

In conclusion, generation of T cells expressing a CAR that comprises a transmembrane domain from a protein that normally transmits an inhibitory signal to immune system cells has been demonstrated. Further, it has been shown that such CAR T cells possess surprising characteristics. In particular, such T cells (i) demonstrate elevated levels of cytokine production in response to stimulation with the antigen to which the extracellular domain of the CAR they express is directed, as compared to T cells expressing CARs that comprise a transmembrane domain from a protein that normally transmits a stimulatory signal to immune system cells; and (ii) are enriched when cultured in the presence of the antigen to which the extracellular domain of the CAR they express is directed, whereas T cells expressing CARs that comprise a transmembrane domain from a protein that normally transmits a stimulatory signal to immune system cells are not enriched to the same extent, when stimulated with the antigen.

EQUIVALENTS

The present disclosure is not to be limited in scope by the specific embodiments described herein. Indeed, various modifications of the subject matter provided herein, in addition to those described, will become apparent to those skilled in the art from the foregoing description. Such modifications are intended to fall within the scope of the appended claims.

Various publications, patents and patent applications are cited herein, the disclosures of which are incorporated by reference in their entireties.

What is claimed is:

1. A method of treating an individual who has tumor cells, comprising administering to the individual a therapeutically effective amount of T lymphocytes expressing a polypeptide comprising (i) a transmembrane domain from PD-1, (ii) a CD3ζ intracellular signaling domain, and (iii) an extracellular domain that binds to an antigen on the tumor cells, wherein the extracellular domain is an antibody or an antigen-binding portion thereof, and wherein the intracellular domain and the extracellular domain of the polypeptide are not from PD-1, such that the tumor cells are killed.

2. The method of claim 1, wherein the polypeptide is a chimeric antigen receptor (CAR).

3. The method of claim 1, wherein the T lymphocytes expressing the polypeptide are stimulated to proliferate when the polypeptide binds to the antigen.

4. The method of claim 1, wherein the antigen is a tumor-associated antigen or a tumor-specific antigen.

5. The method of claim 4, wherein the tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, an abnormal p53 protein, integrin αvβ3 (CD61), galactin, K-Ras (V-Ki-ras2 Kirsten rat sarcoma viral oncogene), or Ral-B.

6. The method of claim 4, wherein the tumor-associated antigen or tumor-specific antigen is BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXB1, SPA17, SSX, SYCP1, TPTE, fuc-GM1, GM2 (oncofetal antigen-immunogenic-1), GM3, GD3, alpha-actinin-4, Bage-1, BCR-ABL, Bcr-Abl fusion protein, beta-catenin, CA 15-3, CA 195, CA 242, CA-50, CAM43, Casp-8, cdc27, cdk4, cdkn2a, coa-1, dek-can fusion protein, EBNA, EF2, Epstein Barr virus antigen, ETV6-AML1 fusion protein, HLA-A2, HLA-A11, hsp70-2, KIAAO205, Mart2, Mum-1, 2, and 3, neo-PAP, myosin class I, OS-9, pml-RARα fusion protein, PTPRK, N-ras, triosephosphate isomerase, Gage 3,4,5,6,7, GnTV, Herv-K-mel, Lage-1, NA-88, NY-Eso-1/Lage-2, SSX-2, TRP2-Int2, gp100 (Pmel 17), TRP-1, TRP-2, MAGE-1, MAGE-3, RAGE, GAGE-1, GAGE-2, SCP-1, Hom/Mel-40, PRAME, p53, H-Ras, E2A-PRL, H4-RET, IGH-IGK, MYL-RAR, human papillomavirus (HPV) antigen E6, HPV antigen E7, TSP-180, MAGE-4, MAGE-5, MAGE-6, p185erbB2, p180erbB-3, c-met, nm-23H1, PSA, TAG-72-4, CA 72-4, CAM 17.1 antigen, NuMa, Mum-1, p16, TAGE, PSMA, CT7, telomerase, 43-9F, 5T4, 791Tgp72, β-HCG, BCA225, BTAA, CD68\KP1, CO-029, FGF-5, G250, Ga733 (EpCAM), HTgp-175, M344, MA-50, MG7-Ag, Ca-MOv18, NB\70K, NY-CO-1, RCAS1, SDCCAG16, TA-90, TAAL6, TAG72, TLP, or TPS.

7. The method of claim 1, wherein the polypeptide additionally comprises one or more co-stimulatory domains, wherein the one or more co-stimulatory domains comprises one or more of: a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, and a co-stimulatory inducible T-cell costimulatory (ICOS) polypeptide sequence.

8. The method of claim 1, wherein the polypeptide comprises, in order, from N-terminus to C terminus: (i) the extracellular domain that binds to an antigen on the tumor cell; (ii) a hinge polypeptide sequence from CD28 or CTLA4; (iii) the transmembrane domain from PD-1; (iv) a costimulatory domain; and (v) the CD3 intracellular signaling domain.

9. The method of claim 8, wherein the polypeptide comprises, in order, from N-terminus to C-terminus: (i) a single-chain Fv domain comprising a $V_L$ linked to $V_H$ by a flexible linker, wherein the $V_L$ and $V_H$ are from an antibody that binds the antigen; (ii) a hinge polypeptide sequence from CD28; (iii) the transmembrane domain from PD-1; (iv) a CD28 costimulatory domain; and (v) the CD3 intracellular signaling domain.

10. The method of claim 8, wherein the polypeptide comprises, in order, from N-terminus to C-terminus: (i) a single-chain Fv domain comprising a $V_L$ linked to $V_H$ by a flexible linker, wherein the $V_L$ and $V_H$ are from an antibody that binds the antigen; (ii) a hinge polypeptide sequence from CTLA4; (iii) the transmembrane domain from PD-1; (iv) a CD28 costimulatory domain; and (v) the CD3ζ intracellular signaling domain.

11. The method of claim 1, wherein the tumor cells are cells of a lymphoma, a lung cancer, a breast cancer, a prostate cancer, an adrenocortical carcinoma, a thyroid carcinoma, a nasopharyngeal carcinoma, a melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, or a lipoma.

12. The method of claim 11, wherein the lymphoma is chronic lymphocytic leukemia, B-cell prolymphocytic leukemia, lymphoplasmacytic lymphoma, Waldenstrom macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

\* \* \* \* \*

SEQUENCE LISTING

```
<160> NUMBER OF SEQ ID NOS: 11

<210> SEQ ID NO 1
<211> LENGTH: 36
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 1

Pro Glu Pro Cys Pro Asp Ser Asp Phe Leu Leu Trp Ile Leu Ala Ala
1               5                   10                  15

Val Ser Ser Gly Leu Phe Phe Tyr Ser Phe Leu Leu Thr Ala Val Ser
            20                  25                  30

Leu Ser Lys Met
        35

<210> SEQ ID NO 2
<211> LENGTH: 29
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 2

Pro Asp Ser Asp Phe Leu Leu Trp Ile Leu Ala Ala Val Ser Ser Gly
1               5                   10                  15

Leu Phe Phe Tyr Ser Phe Leu Leu Thr Ala Val Ser Leu
            20                  25

<210> SEQ ID NO 3
<211> LENGTH: 23
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 3

Phe Leu Leu Trp Ile Leu Ala Ala Val Ser Ser Gly Leu Phe Phe Tyr
1               5                   10                  15

Ser Phe Leu Leu Thr Ala Val
            20
```

```
<210> SEQ ID NO 4
<211> LENGTH: 21
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 4

Phe Leu Leu Trp Ile Leu Ala Ala Val Ser Ser Gly Leu Phe Phe Tyr
1               5                   10                  15

Ser Phe Leu Leu Thr
            20

<210> SEQ ID NO 5
<211> LENGTH: 26
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 5

Phe Leu Leu Trp Ile Leu Val Ala Val Ser Leu Gly Leu Phe Phe Tyr
1               5                   10                  15

Ser Phe Leu Val Ser Ala Val Ser Leu Ser
            20                  25

<210> SEQ ID NO 6
<211> LENGTH: 29
<212> TYPE: PRT
<213> ORGANISM: Artificial Sequence
<220> FEATURE:
<223> OTHER INFORMATION: synthetic peptide - PD-1 transmembrane domain

<400> SEQUENCE: 6

Thr Leu Val Val Gly Val Val Gly Gly Leu Leu Gly Ser Leu Val Leu
1               5                   10                  15

Leu Val Trp Val Leu Ala Val Ile Cys Ser Arg Ala Ala
            20                  25

<210> SEQ ID NO 7
<211> LENGTH: 21
<212> TYPE: PRT
<213> ORGANISM: Artificial Sequence
<220> FEATURE:
<223> OTHER INFORMATION: synthetic peptide - PD-1 transmembrane domain

<400> SEQUENCE: 7

Val Gly Val Val Gly Gly Leu Leu Gly Ser Leu Val Leu Leu Val Trp
1               5                   10                  15

Val Leu Ala Val Ile
            20

<210> SEQ ID NO 8
<211> LENGTH: 26
<212> TYPE: PRT
<213> ORGANISM: Artificial Sequence
<220> FEATURE:
<223> OTHER INFORMATION: synthetic peptide - PD-1 transmembrane domain

<400> SEQUENCE: 8

Phe Gln Thr Leu Val Val Gly Val Val Gly Gly Leu Leu Gly Ser Leu
1               5                   10                  15

Val Leu Leu Val Trp Val Leu Ala Val Ile
```

```
<210> SEQ ID NO 9
<211> LENGTH: 49
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 9

Leu Gly Ile Gly Asn Gly Thr Gln Ile Tyr Val Ile Asp Pro Glu Pro
1               5                   10                  15

Ser Pro Asp Ser Asp Phe Leu Leu Trp Ile Leu Ala Ala Val Ser Ser
            20                  25                  30

Gly Leu Phe Phe Tyr Ser Phe Leu Leu Thr Ala Val Ser Leu Ser Lys
        35                  40                  45

Met

<210> SEQ ID NO 10
<211> LENGTH: 28
<212> TYPE: PRT
<213> ORGANISM: Artificial Sequence
<220> FEATURE:
<223> OTHER INFORMATION: synthetic peptide - CTLA4 transmembrane domain

<400> SEQUENCE: 10

Phe Leu Leu Trp Ile Leu Ala Ala Val Ser Ser Gly Leu Phe Phe Tyr
1               5                   10                  15

Ser Phe Leu Leu Thr Ala Val Ser Leu Ser Lys Met
            20                  25

<210> SEQ ID NO 11
<211> LENGTH: 31
<212> TYPE: PRT
<213> ORGANISM: Artificial Sequence
<220> FEATURE:
<223> OTHER INFORMATION: synthetic peptide - PD-1 transmembrane domain

<400> SEQUENCE: 11

Phe Gln Thr Leu Val Val Gly Val Val Gly Gly Leu Leu Gly Ser Leu
1               5                   10                  15

Val Leu Leu Val Trp Val Leu Ala Val Ile Cys Ser Arg Ala Ala
            20                  25                  30
```